(12) United States Patent
Chen et al.

(10) Patent No.: US 10,835,244 B2
(45) Date of Patent: Nov. 17, 2020

(54) TISSUE CLOSURE DEVICE, TISSUE CLOSURE COMPONENT, AND MEDICAL INSTRUMENT

(71) Applicant: TOUCHSTONE INTERNATIONAL MEDICAL SCIENCE CO., LTD., Suzhou (CN)

(72) Inventors: Wangdong Chen, Suzhou (CN); Kezhan Sun, Suzhou (CN); Jiang Lin, Suzhou (CN); Yi Guo, Suzhou (CN); Yuanyang Cao, Suzhou (CN); Rongqiong Zhang, Suzhou (CN)

(73) Assignee: TOUCHSTONE INTERNATIONAL MEDICAL SCIENCE CO., LTD., Suzhou (CN)

( * ) Notice: Subject to any disclaimer, the term of this patent is extended or adjusted under 35 U.S.C. 154(b) by 247 days.

(21) Appl. No.: 16/061,641

(22) PCT Filed: Dec. 22, 2016

(86) PCT No.: PCT/CN2016/111459
§ 371 (c)(1),
(2) Date: Jun. 12, 2018

(87) PCT Pub. No.: WO2017/107947
PCT Pub. Date: Jun. 29, 2017

(65) Prior Publication Data
US 2020/0155148 A1    May 21, 2020

(30) Foreign Application Priority Data
Dec. 22, 2015  (CN) .......................... 2015 1 0974519
Aug. 8, 2016   (CN) .......................... 2016 1 0642767
(Continued)

(51) Int. Cl.
*A61B 17/064* (2006.01)
*A61B 17/068* (2006.01)
(Continued)

(52) U.S. Cl.
CPC ...... *A61B 17/0686* (2013.01); *A61B 17/0644* (2013.01); *A61B 17/072* (2013.01);
(Continued)

(58) Field of Classification Search
CPC .............. A61B 17/128; A61B 17/0686; A61B 2017/00473
(Continued)

(56) References Cited

U.S. PATENT DOCUMENTS 3,006,344 A  * 10/1961  Vogelfanger ....... A61B 17/1285
                                                        606/143
3,079,608 A  *  3/1963  Ivanovich ............ A61B 17/128
                                                        29/243.57
(Continued)

FOREIGN PATENT DOCUMENTS

CN    101669834 A    3/2010
CN    104248459 A   12/2014
(Continued)

*Primary Examiner* — Andrew M Tecco
*Assistant Examiner* — Eyamindae C Jallow
(74) *Attorney, Agent, or Firm* — Seed IP Law Group LLP

(57) ABSTRACT

The present invention discloses a tissue closure device, a tissue closure assembly and a medical instrument. The tissue closure device comprises a base, a pressure plate cooperating with the base, and a staple pushing sheet. The pressure plate is rotatable relatively to the base. The tissue closure device further comprises a staple accommodating portion which is arranged at the distal end of the base and configured to accommodate a closure staple. The staple pushing sheet and the staple accommodating portion are configured to cooperatively drive the closure staple in the staple accom-
(Continued)

modating portion to deform. In the present invention, a bundled pouch with a gathered center is formed through the tissue closure device, so that risks of stoma fistula arising from subsequent anastomosis through a circular stapler are reduced; and the surgery cost is reduced.

29 Claims, 14 Drawing Sheets

(30) Foreign Application Priority Data

| | | |
|---|---|---|
| Aug. 8, 2016 | (CN) | 2016 1 0642768 |
| Aug. 8, 2016 | (CN) | 2016 2 0850795 U |
| Aug. 8, 2016 | (CN) | 2016 2 0853858 U |

(51) Int. Cl.
  *A61B 17/072* (2006.01)
  *A61B 17/00* (2006.01)

(52) U.S. Cl.
  CPC ............ *A61B 2017/00473* (2013.01); *A61B 2017/0641* (2013.01); *A61B 2017/07228* (2013.01); *A61B 2017/07285* (2013.01)

(58) Field of Classification Search
  USPC .................. 227/901, 902; 606/151, 157
  See application file for complete search history.

(56) References Cited

U.S. PATENT DOCUMENTS

| | | | | |
|---|---|---|---|---|
| 3,545,444 | A * | 12/1970 | Green | A61B 17/128 606/143 |
| 3,584,628 | A * | 6/1971 | Green | A61B 17/128 606/143 |
| 3,683,927 | A | 8/1972 | Noiles | |
| 5,221,036 | A | 6/1993 | Takase | |
| 5,431,669 | A * | 7/1995 | Thompson | A61B 17/1285 227/902 |
| 5,601,573 | A * | 2/1997 | Fogelberg | A61B 17/1227 606/143 |
| 5,681,330 | A * | 10/1997 | Hughett | A61B 17/1285 606/143 |
| 5,769,857 | A * | 6/1998 | Reztzov | A61B 17/1285 606/139 |
| 5,858,018 | A * | 1/1999 | Shipp | A61B 17/1227 606/142 |
| 6,241,740 | B1 * | 6/2001 | Davis | A61B 17/1285 606/139 |
| 6,350,269 | B1 * | 2/2002 | Shipp | A61B 17/1227 606/143 |
| 8,652,152 | B2 * | 2/2014 | Aranyi | A61B 17/1285 606/143 |
| 8,900,253 | B2 * | 12/2014 | Aranyi | A61B 17/122 606/142 |
| 10,111,660 | B2 * | 10/2018 | Hemmann | A61B 17/068 |
| 2015/0112370 | A1 * | 4/2015 | Euteneuer | A61B 17/068 606/151 |
| 2016/0100835 | A1 * | 4/2016 | Linder | A61B 17/0644 606/220 |

FOREIGN PATENT DOCUMENTS

| | | |
|---|---|---|
| CN | 106137289 A | 11/2016 |
| CN | 106175861 A | 12/2016 |

* cited by examiner

TISSUE CLOSURE DEVICE, TISSUE CLOSURE COMPONENT, AND MEDICAL INSTRUMENT

This application claims the priority of the Chinese patent application No. 201610642768.8, titled as "TISSUE CLOSURE ASSEMBLY AND MEDICAL INSTRUMENT EQUIPPED WITH SAME" and filed on Aug. 8, 2016, the Chinese patent application No. 201610642767.3, titled as "TISSUE CLOSURE DEVICE, TISSUE CLOSURE ASSEMBLY AND MEDICAL INSTRUMENT EQUIPPED WITH THE TISSUE CLOSURE ASSEMBLY" and filed on Aug. 8, 2016, the Chinese patent application No. 201620850795.X, titled as "TISSUE CLOSURE ASSEMBLY AND CLOSURE STAPLE THEREFOR, AND MEDICAL INSTRUMENT" and filed on Aug. 8, 2016, the Chinese patent application No. 201510974519.4, titled as "TISSUE CLOSURE DEVICE, TISSUE CLOSURE ASSEMBLY AND MEDICAL INSTRUMENT EQUIPPED WITH THE TISSUE CLOSURE DEVICE" and filed on Dec. 22, 2015, and the Chinese patent application No. 201620853858.7, titled as "TISSUE CLOSURE ASSEMBLY AND CLOSURE STAPLE THEREFOR, AND MEDICAL INSTRUMENT" and filed on Aug. 8, 2016, which are incorporated herein by reference in their entireties.

TECHNICAL FIELD

The present invention relates to the technical field of medical instruments, and more particularly, to a tissue closure device, a tissue closure assembly and a medical instrument.

BACKGROUND

In an existing digestive tract anastomosis surgery, a linear cutter stapler or arcuate stapler is generally used firstly for performing multi-angle resection and anastomosis on tubular tissues, and then anastomosis of the tubular tissues are carried out using a circular stapler.

However, after the tubular tissues being performed resection and anastomosis with the linear cutter stapler or arcuate stapler, a cross-staple phenomenon will appear due to continuous linear staple lines on the anastomosis stoma, especially, due to the limitations of both a human pelvic floor operation space and the swing angle of the linear stapler when the surgery is performed at a lower rectum position. As a result, "dog ears" cannot be avoided when the circular stapler is used to perform the anastomisis of tissues. Thus, under such circumstances, the surgery has a higher risk of stoma fistula. and the surgery costs are much higher.

SUMMARY

Objects of the present invention are to provide a tissue closure device, a tissue closure assembly and a medical instrument.

In order to achieve one of the above objects, an embodiment of the present invention provides a tissue closure device comprising a base, a pressure plate cooperating with the base, and a staple pushing sheet.

The pressure plate is rotatable relatively to the base, and comprises an open position and a closure position. When the pressure plate is located at the closure position, the pressure plate cooperates with the base to form a first accommodating space for accommodating part of a tubular tissue.

The staple pushing sheet comprises an original position and a staple closure position. The original position is located at the proximal end of the staple closure position and the first accommodating space.

The tissue closure device further comprises a staple accommodating portion which is arranged at the distal end of the base and configured to place at least one closure staple. The staple pushing sheet and the staple accommodating portion are configured to cooperatively drive the closure staple located in the staple accommodating portion to deform.

As a further improvement of an embodiment of the present invention, a second accommodating space is formed in the staple accommodating portion, which is communicated with the first accommodating space, the height of the second accommodating space is bigger than the height of the first accommodating space.

As a further improvement of an embodiment of the present invention, the staple accommodating portion and the base are integrally formed; and the inner bottom wall of the staple accommodating portion smoothly transits to the inner bottom wall of the base.

As a further improvement of an embodiment of the present invention, the second accommodating space comprises at least one staple accommodating groove. Each staple accommodating groove can accommodate at least part of the closure staple to fix a relative position between the closure staple and the staple accommodating portion.

As a further improvement of an embodiment of the present invention, during the process that the staple pushing sheet moves from the original position to the staple closure position, the tubular tissue in the first accommodating space is gradually gathered towards the second accommodating space and is totally accommodated in the second accommodating space finally.

As a further improvement of an embodiment of the present invention, the distal end surface of the staple pushing sheet is an arcuate deforming groove.

During the process that the staple pushing sheet moves from the original position to the staple closure position, the arcuate end of the deforming groove is in contact with the closure staple first, and applies a pressure to an open end of the closure staple in the continuous movement process of the staple pushing sheet so as to bend the open end of the closure staple.

When the staple pushing sheet reaches the staple closure position, the deforming groove forms a third accommodating space to accommodate part of the tubular tissue.

As a further improvement of an embodiment of the present invention, the tissue closure device further comprises a staple case communicating with the staple accommodating groove of the staple accommodating portion. A staple pushing structure is arranged in the staple case to load the closure staple in the staple case into the staple accommodating groove.

As a further improvement of an embodiment of the present invention, the staple case is arranged in the staple accommodating portion.

As a further improvement of an embodiment of the present invention, the staple pushing sheet further comprises a pulling-back position between the original position and the staple closure position. The staple accommodating portion is further configured to place a cutting knife. When the staple pushing sheet moves from the staple closure position to the pulling-back position, the staple pushing sheet cooperates with the cutting knife to drive the cutting knife to move from the distal end of the base to the proximal end thereof so as to cut the tissue.

As a further improvement of the embodiment of the present invention, the staple accommodating portion is further configured to place at least one closure staple. The staple pushing sheet and the staple accommodating portion are configured to cooperatively drive the closure staple located in the staple accommodating portion to form. When the staple pushing structure drives the closure staple to be deformed from the proximal end to the distal end, the cutting knife is motionless relative to the staple accommodating portion, so as not to cut the tissue.

As a further improvement of the embodiment of the present invention, there are two closure staples located at the two sides of the cutting knife, respectively.

As a further improvement of the embodiment of the present invention, the staple accommodating portion is provided with a step to limit the movement of the closure staple towards a proximal end direction. When the staple pushing sheet engages with the cutting knife and drives the cutting knife to move towards the proximal end, the closure staple remains motionless relative to the staple accommodating portion.

As a further improvement of the embodiment of the present invention, the staple pushing sheet is provided with a staple deforming groove for forming the closure staple and side walls for compressing the tissue; and the side walls are higher than the staple deforming groove.

As a further improvement of the embodiment of the present invention, the staple pushing sheet is provided with a middle wall between the side walls; and the middle wall is lower than the side walls.

As a further improvement of the embodiment of the present invention, the middle wall is provided with an arcuate recess portion.

As a further improvement of the embodiment of the present invention, the cutting knife comprises a cutting portion for cutting the tissue, as well as a first connection portion and a second connection portion which are respectively located at the two opposite sides of the cutting portion and are connected with the cutting portion. The first and second connection portions selectively disengage from or engage with the staple pushing sheet.

As a further improvement of the embodiment of the present invention, the cutting portion is provided with a halberd blade for cutting off the tissue; and the halberd blade is provided with a tip portion.

As a further improvement of the embodiment of the present invention, the cutting portion is further provided with oblique blades for slidably cutting off side walls of the tissue. Each oblique blade extends along a curve, and is smoothly connected with the halberd blade. There are two oblique blades distributed at the two sides of the halberd blade, respectively.

As a further improvement of the embodiment of the present invention, each of the first and second connection portions is provided with a cooperation portion; and the staple pushing sheet is provided with an engagement portion which selectively disengages from or engages with the cooperation portion.

As a further improvement of the embodiment of the present invention, the cooperation portion is a clasp; and the engagement portion is a protrusion.

As a further improvement of the embodiment of the present invention, the cutting knife is provided with a cooperation portion. The staple pushing sheet is provided with an engagement portion which selectively disengages from or engages with the cooperation portion. When the staple pushing sheet moves from the staple closure position to the pulling-back position, the cooperation portion cooperates with the engagement portion to enable the staple pushing sheet to drive the cutting knife to move from the distal end of the base to the proximal end, so as to cut off the tissue. When the staple pushing sheet moves from the original position to the staple closure position, the cooperation portion disengages from the engagement portion.

As a further improvement of the embodiment of the present invention, the cooperation portion is a clasp; and the engagement portion is a protrusion.

In order to achieve one of the above objects, an embodiment of the present invention provides a tissue closure assembly comprising: the tissue closure device described in the above technical solutions, and a closure staple capable of being assembled to the tissue closure device. The tissue closure assembly further comprises a cutting knife which is assembled to the tissue closure device and which selectively disengages from or engages with the staple pushing sheet. At the original position, the staple pushing sheet disengages from the cutting knife; and at the staple closure position, the staple pushing sheet cooperates with the cutting knife.

In order to achieve one of the above objects, an embodiment of the present invention further provides another tissue closure assembly comprising: the tissue closure device described in the above technical solutions, and a closure staple capable of being assembled to the tissue closure device. During a closure process, when the staple pushing sheet is located at the original position, the free end of the closure staple is opposite to the staple pushing sheet. When the staple pushing sheet is located at the staple closure position, the free end of the closure staple is bent under the action of the staple pushing sheet.

As a further improvement of an embodiment of the present invention, the closure staple is provided with an opening portion, a bottom opposite to the opening portion, and a side wall connected to the bottom; and the end of the side wall is spike-shaped.

As a further improvement of an embodiment of the present invention, at least one spike-shaped portion is arranged on the bottom of the closure staple.

As a further improvement of an embodiment of the present invention, at least one barb whose end point faces to the bottom of the closure staple is arranged on the side wall of the closure staple.

As a further improvement of an embodiment of the present invention, the closure staple comprises a base portion, a connection portion connected with the base portion, as well as a first side portion and a second side portion which are connected with the connection portion and are located at the two sides of the connection portion, respectively; an opening is formed between the first side portion and the second side portion; and the base portion constitutes a closed channel allowing an instrument to pass through.

As a further improvement of an embodiment of the present invention, each of the first side portion and the second side portion is provided with a thorn portion.

As a further improvement of an embodiment of the present invention, the thorn portion extends in a direction towards the connection portion.

As a further improvement of an embodiment of the present invention, there are multiple thorn portions.

As a further improvement of an embodiment of the present invention, three thorn portions are arranged on each of the first and second side portions; and the thorn portions on the first and second side portions are symmetrical.

As a further improvement of an embodiment of the present invention, the closed channel is a circular channel.

As a further improvement of an embodiment of the present invention, a spike-shaped portion is arranged on the connection portion.

As a further improvement of an embodiment of the present invention, the centers of both the connection portion and the closed channel define a center line; and two spike-shaped portions are symmetrically arranged on the connection portion with respect to the center line.

As a further improvement of an embodiment of the present invention, an extension rod is further arranged on the base portion; and the extension rod and the connection portion are located at the two opposite sides of the base portion.

As a further improvement of an embodiment of the present invention, the extension rod is provided with a spike-shaped end.

As a further improvement of an embodiment of the present invention, there are three extension rods, wherein an extension line of a first extension rod passes through the center of the base portion, and the other two extension rods are symmetrical with respect to the first extension rod.

As a further improvement of an embodiment of the present invention, the closure staple comprises a first side portion, a second side portion opposite to the first side portion, and a bottom connected with the first and second side portions. An opening portion is formed between the first side portion and the second side portion. The bottom is opposite to the opening portion; and at least one thorn is arranged on the bottom.

As a further improvement of an embodiment of the present invention, the first end of the thorn is arranged on the bottom; and the second end of the thorn is a tail end. A perpendicular line is defined through the tail end of the thorn and is perpendicular to the thorn. After the closure staple is bent and formed, bending portions of both the first and second side portions intersect with the perpendicular line.

As a further improvement of an embodiment of the present invention, a first thorn and a second thorn are arranged on the bottom, and are symmetrical to each other.

As a further improvement of an embodiment of the present invention, the first side portion and the second side portion define a first plane. After the closure staple is bent and formed, projections of bending portions of both the first side portion and the second side portion intersect with each other on the first plane.

As a further improvement of an embodiment of the present invention, the first side portion and the second side portion define a first plane. After the closure staple is bent and formed, projections of bending portions of both the first side portion and the second side portion are away from each other on the first plane.

As a further improvement of an embodiment of the present invention, a third thorn is further arranged on the bottom, and said third thorn coincides with a center line of the first side portion and the second side portion.

As a further improvement of an embodiment of the present invention, the first and second thorns are longer than the third thorn.

As a further improvement of an embodiment of the present invention, the third thorn portion is longer than the first and second thorn portions.

In order to achieve one of the above objects, an embodiment of the present invention provides a medical instrument, comprising: an instrument body, and an firing handle connected to the instrument body. The medical instrument further comprises the tissue closure device according to the above technical solutions. The tissue closure device is detachably connected to the instrument body.

Compared with the prior art, the present invention has the following beneficial effects: a bundled pouch with a gathered center is formed through the tissue closure device, so that the risk of "dog ears" and stoma fistula arising from subsequent anastomosis through a circular stapler are reduced; and meanwhile, the operation is simpler, the use is more convenient, and the surgery cost is reduced.

BRIEF DESCRIPTION OF THE DRAWINGS

FIG. 16b is a front view of the closure staple shown in FIG. 16a;

FIG. 17b is a front view of the closure staple shown in FIG. 17a;

DETAILED DESCRIPTION

The present invention will be described in detail below with reference to specific embodiments shown in the accompanying drawings. However, these embodiments are not intended to limit the present invention, and changes of structures, methods or functions, made by an ordinary person skilled in the art in accordance with these embodiments are comprised within the protective scope of the present invention.

In order to clearly express the position and direction described in the present invention, an instrument operator is taken as a reference, the end close to the operator is a proximal end, and the end away from the operator is a distal end.

Figure 1:
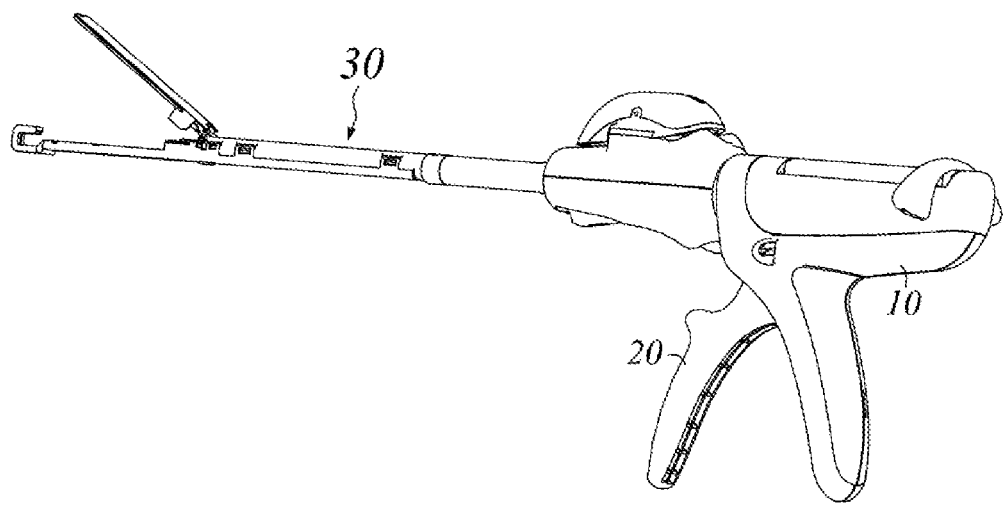
FIG. 1 is a schematically perspective view of a medical instrument according to a first embodiment of the present invention.

As shown in FIG. 1, the present invention discloses an embodiment of a medical instrument. The medical instrument may be used in a digestive tract anastomosis surgery. The medical instrument comprises an instrument body 10, an firing handle 20 pivotally connected to the instrument body 10, and a tissue closure device 30 detachably connected to the instrument body 10. In general, the tissue closure device 30 is arranged at the distal end of the instrument body 10.

The structure of the instrument body 10 may be the same as that of an instrument body of an existing linear or arcuate stapler, or may be designed separately. It can be understood that the structure of the instrument body 10 is only required to cooperate with the tissue closure device 30 to work. In the following description, the structure of the instrument body of the existing linear or arcuate stapler will serve as that of the instrument body 10 in the present embodiment to illustrate.

In addition, the present invention further discloses an embodiment of a tissue closure assembly. The tissue closure assembly comprises a tissue closure device 30 and a closure staple 50 capable of being assembled to the tissue closure device 30. Structures and use manners of both the tissue closure device 30 and the closure staple 50 will be described in detail below.

Figure 2:
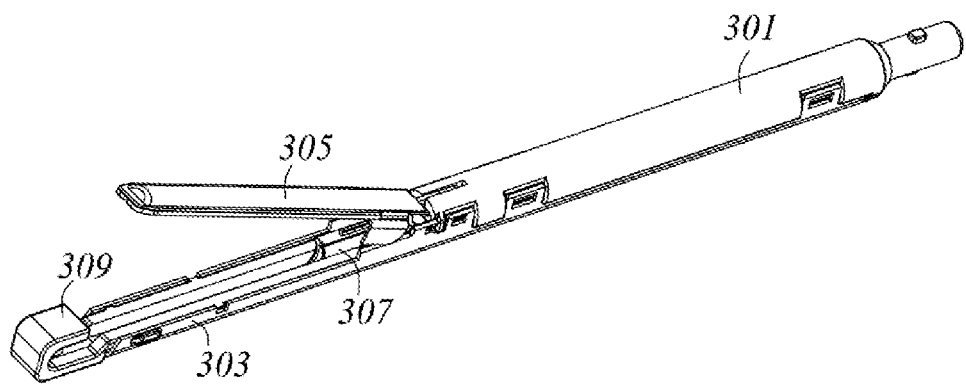
FIG. 2 is a schematically perspective view of a tissue closure device according to the first embodiment of the present invention.
Figure 3:
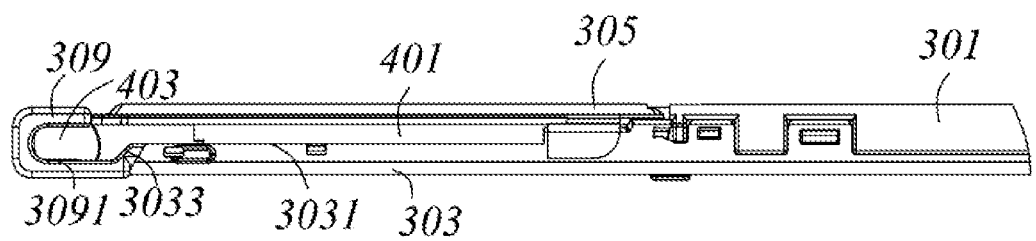
FIG. 3 is a sectional view of the tissue closure device according to the first embodiment of the present invention.

As shown in FIGS. 2 and 3, the tissue closure device 30 comprises a connection portion 301, a base 303, a pressure plate 305 cooperating with the base 303, a staple pushing sheet 307, and a staple accommodating portion 309.

The connection portion 301 is configured to connect the instrument body 10. The base 303 is arranged at the distal end of the connection portion 301, and may be integrally formed with the base of the connection portion 301.

The pressure plate 305 is pivotably connected to the base 303 to enable the pressure plate 305 to rotate relative to the base 303.

The staple accommodating portion 309 is arranged at the distal end of the base 303.

Further, the pressure plate 305 comprises an open position and a closure position. For example, the open and closure positions are two extreme positions or positions close to the extreme positions (caused by an error in the mechanical cooperation process) when the pressure plate 35 pivotally rotates. When the pressure plate 305 is at the closure position, the pressure plate 305 and the base 303 cooperate to form a first accommodating space 401 for accommodating part of a tubular tissue. The first accommodating space 401 is a cavity with two open ends. During surgery, a tubular tissue (e.g., an intestinal tract, etc.) may be received at the open position. At the closure position, part of the tubular tissue is located between the pressure plate 305 and the base 303.

Figure 6A:
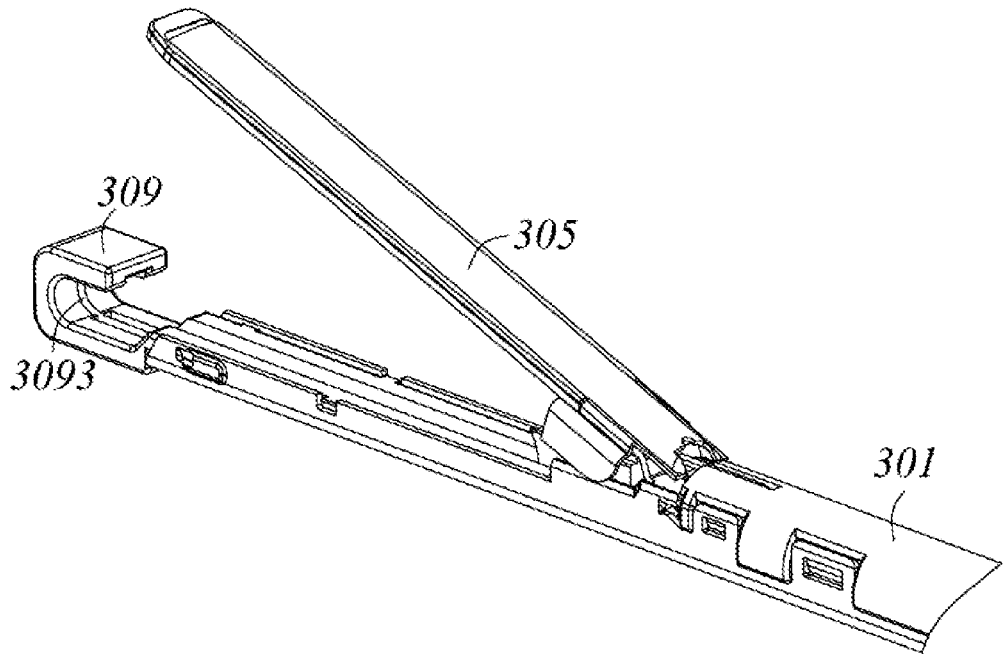
FIG. 6a is a schematically perspective view of the tissue closure device in which a pressure plate is at an open position according to the first embodiment of the present invention.
Figure 6B:
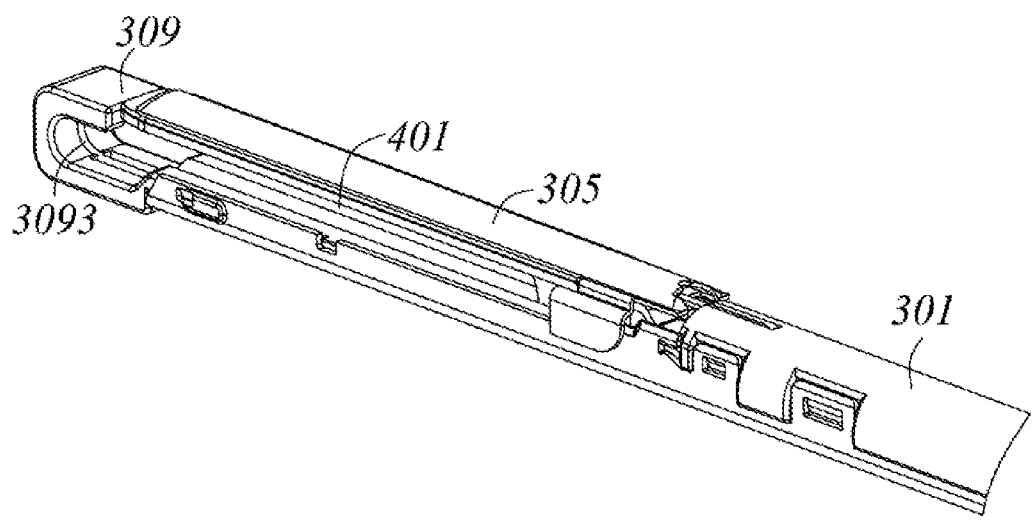
FIG. 6b is a schematically perspective view of the tissue closure device in which the pressure plate is at a closure position according to the first embodiment of the present invention.

Further, the staple pushing sheet 307 comprises an original position and a staple closure position. The original position is located at the proximal end of the staple closure position and the first accommodating space 401 (as shown in FIG. 6a). In general, when being at the original position, the staple pushing sheet 307 acts on the distal end of the pressure plate 305 and is away from the base 303, so as to reach the open position of the pressure plate 305. When moving from the original position to the staple closure position, the staple pushing sheet 307 acts on the distal end of the pressure plate 305 and is close to the base 303, so as to reach the closure position (as shown in FIG. 6b) of the pressure plate 305. The working principle of the staple pushing sheet may refer to a cooperation structure of an I-shaped knife, a staple cartridge and a staple anvil of a linear or arcuate stapler, which will not be repeated herein.

Further, the staple accommodating portion 309 may be configured to accommodate at least one closure staple. The staple pushing sheet 307 and the staple accommodating portion 309 are configured to cooperatively drive the closure staple located in the staple accommodating portion 309 to deform.

Figure 6C:
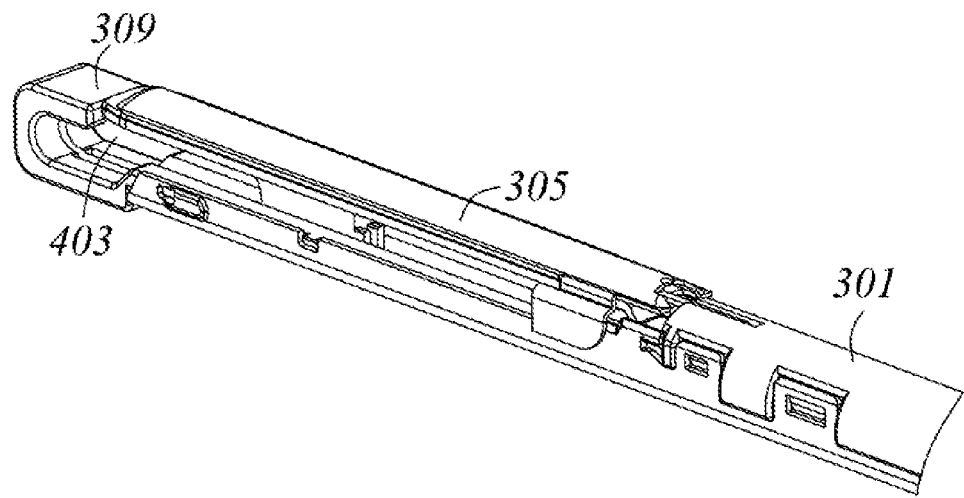
FIG. 6c is a schematically perspective view of the tissue closure device in which a staple pushing sheet moves from an original position to a staple closure position according to the first embodiment of the present invention.

The staple pushing sheet 307 may have various shapes only if it can cooperate with the staple accommodating portion to drive the closure staple to deform so as to complete the closure of the tissue. In an embodiment, the distal end surface of the staple pushing sheet 307 in an embodiment is a planar deforming groove, so that when the staple pushing sheet 307 moves from the original position to the staple closure position (as shown in FIG. 6c), the tubular tissue arranged in the first accommodating space 401 is gradually gathered towards the second accommodating space 403 and is totally accommodated in the second accommodating space 403 finally. It can be understood that, during the surgery, when the staple pushing sheet 307 is at the original position, no matter whether the tubular tissue is accommodated in both the first accommodating space 401 and the second accommodating space 403 or is only accommodated in the first accommodating space 401, the tubular tissue in the first accommodating space 401 will be pushed into the second accommodating space 403 during the process that the staple pushing sheet moves from the original position to the staple closure position, so that when the staple pushing sheet 307 reaches the staple closure position, the tubular tissue gathered in the second accommodating space 403 will be bundled into a pouch.

Figure 6D:
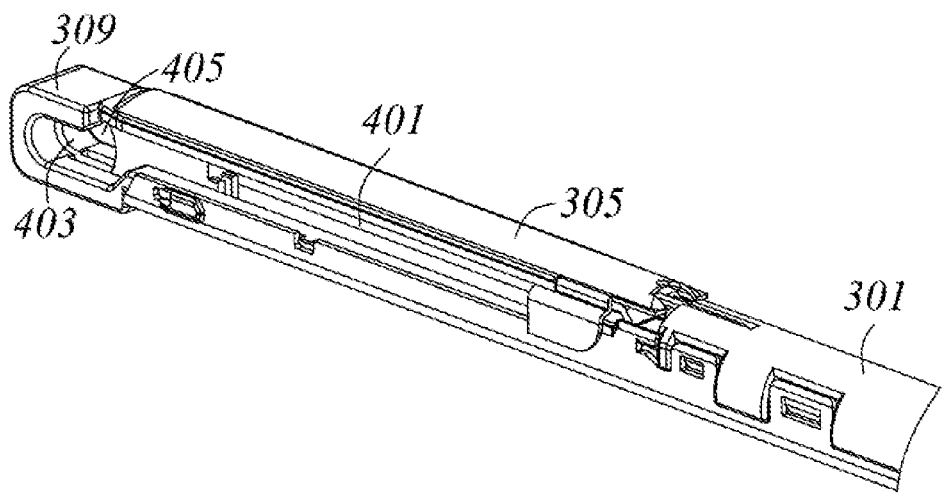
FIG. 6d is a schematically perspective view of the tissue closure device in which the staple pushing sheet reaches a staple closure position according to the first embodiment of the present invention.

In another embodiment, the distal end surface of the staple pushing sheet 307 may be an arcuate deforming groove. Thus, during the process that the staple pushing sheet 307 moves from the original position to the staple closure position, the arcuate end of the deforming groove is in contact with the closure staple first, and applies a pressure to the open end of the closure staple 50 during the continuous movement of the staple pushing sheet 307 to bend the open end of the closure staple 50, so as to bundle the gathered tubular tissue into a pouch. The deforming groove may form a third accommodating space 405 to accommodate part of the tubular structure. When the pushing staple sheet 307 reaches the staple closure position, the third accommodating space 405 may seal the second accommodating space 403 in the axial direction of the tissue closure device (as shown in FIG. 6d), so that the size of the accommodating spaces of the tubular tissue is increased. It can be understood that the third accommodating space 405 is actually a part of the first accommodating space 401.

It can be understood that if the deforming groove of the staple pushing sheet has different shapes, the shape of a formed staple also changes accordingly. For example, the shape of the staple after closure may be "B"-shaped.

In an embodiment of the present invention, the staple accommodating portion 309 forms a second accommodating space 403 which is communicated with the first accommodating space 401. That is, the opening of the second accommodating space 403 faces to the staple pushing sheet 307. The height of the second accommodating space 403 is bigger than the height of the first accommodating space 401. That is, the distance from the base 303 to the pressure plate 305 is less than the aperture of the opening of the second accommodating space 403.

Further, the staple accommodating portion 309 and the base 303 are integrally formed; and the inner bottom wall 3091 of the staple accommodating portion smoothly transits to the inner bottom wall 3031 of the base through an arcuate or inclined surface 3033.

In the present embodiment, the cross section of the staple accommodating portion 309 is U-shaped.

Figure 4:
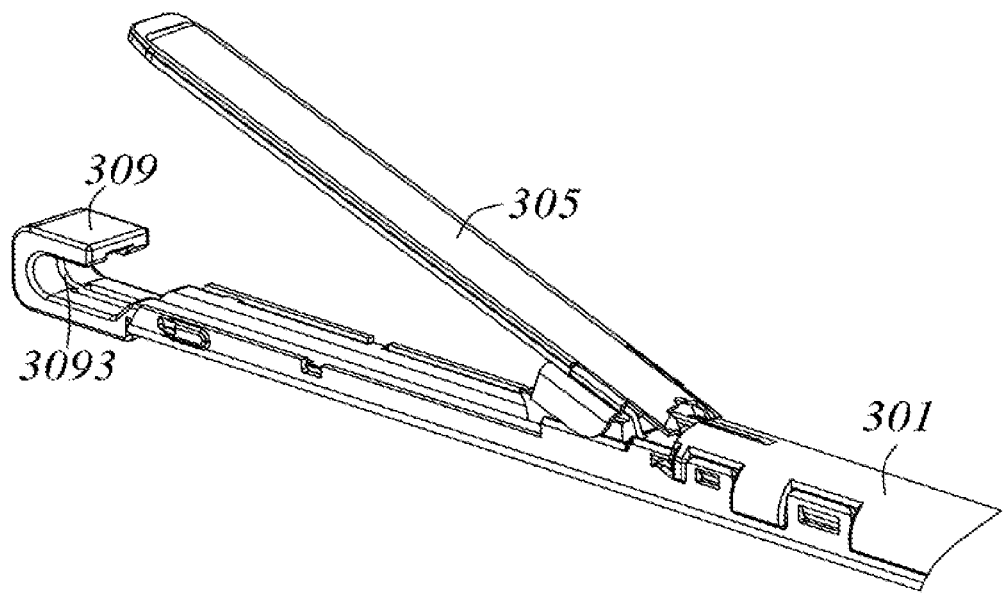
FIG. 4 is a schematically perspective view of the tissue closure device according to the first embodiment of the present invention.
Figure 5:
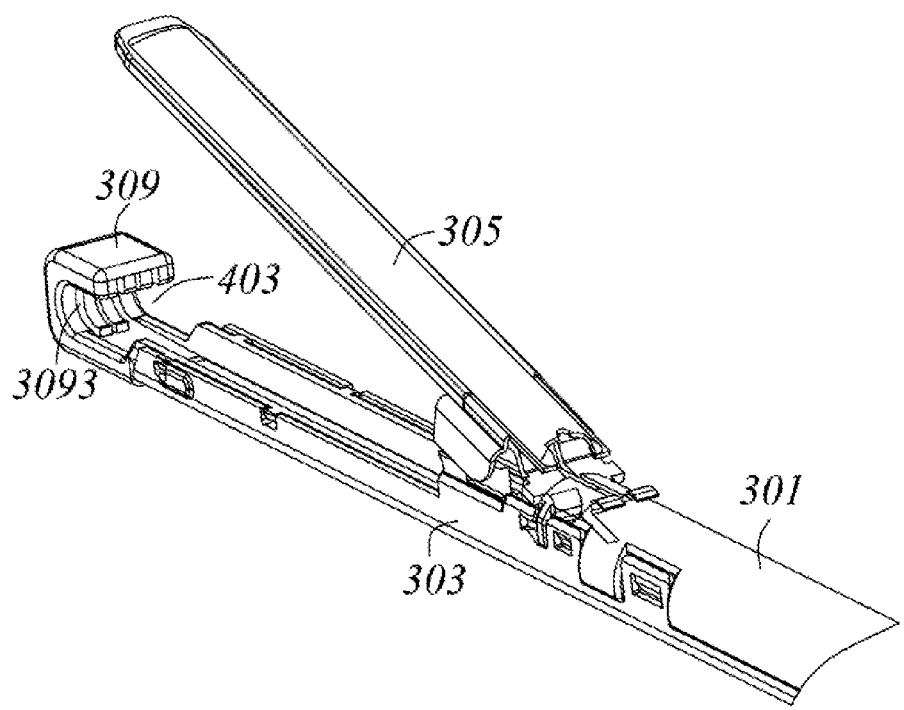
FIG. 5 is a schematically perspective view of a tissue closure device according to a second embodiment of the present invention.

As shown in FIGS. 4 and 5, FIG. 4 shows an example in which only one closure staple may be accommodated into the staple accommodating portion once; and FIG. 5 shows a second embodiment in which two closure staples may be accommodated into the staple accommodating portion once. The second accommodating space 403 comprises at least one staple accommodating groove 3093. The staple accommodating groove 3093 may be formed by the inner wall of the staple accommodating portion 309, or may be arranged on the inner wall of the staple accommodating portion 309.

Further, the tissue closure device 30 further comprises a staple case communicating with the staple accommodating groove 3093 of the staple accommodating portion 309. A staple pushing structure (for example, a return spring) is arranged in the staple case to load a closure staple in the staple case into the staple accommodating groove 3093. Therefore, once there is no closure staple in the staple accommodating groove 3093 (for example, after the firing is completed and the tissue is taken out), another closure staple will be automatically loaded into the staple accommodating groove 3093.

Further, the staple case is arranged in the staple accommodating portion 309. For example, the staple case may be arranged in a body of the staple accommodating portion 309 opposite to the opening of the staple accommodating portion. Of course, the staple case may be movably connected to the staple accommodating portion 309 to facilitate the replacement and loading of the closure staple.

Figure 7A:
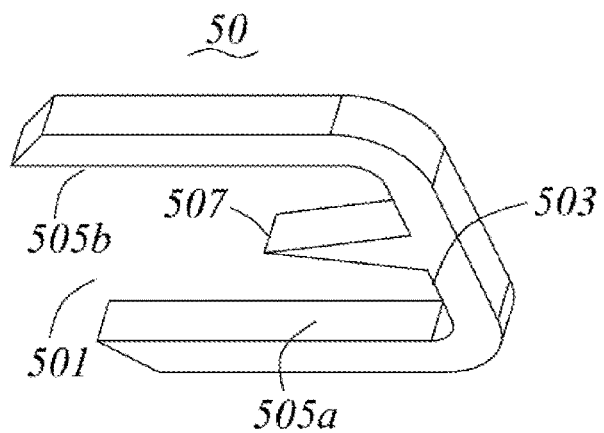
FIG. 7a is a schematically perspective view of a closure staple according to the first embodiment of the present invention.

As shown in FIG. 7a, in an embodiment of the present invention, a closure staple 50 in the tissue closure assembly is provided with an opening portion 501, a bottom 503 opposite to the opening portion, and side walls 505a and 505b connected to the bottom. The side walls 505a and 505b form the free end of the closure staple 50.

In the present embodiment, the ends of the side walls 505a and 505b are spike-shaped so as to pierce through the gathered tubular tissue for closure.

During a closure process, when the staple pushing sheet 307 is at the original position, the free end of the closure staple 50 is opposite to the staple pushing sheet 307. When the staple pushing sheet 307 is at the staple closure position, the free end of the closure staple 50 pierces through the gathered tubular tissue and is bent under the action of the staple pushing sheet, so as to form a closure shape as shown in FIG. 7b.

Figure 7B:
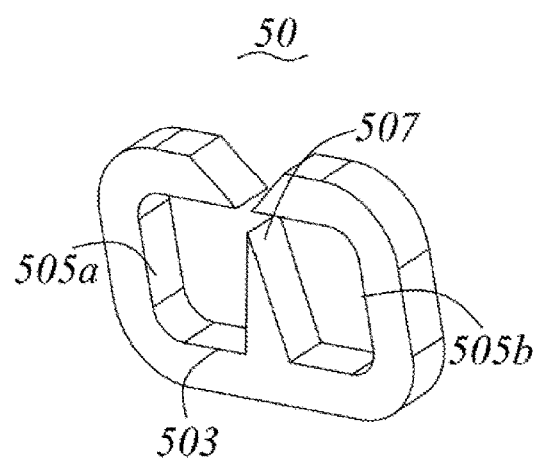
FIG. 7b is a schematically perspective view of the closure staple shown in FIG. 7a after being bent.

Further, at least one spike-shaped portion 507 is arranged on the bottom 503 of the closure staple 50 (FIG. 7a or 7b illustrates a case where one spike-shaped portion is provided) to increase the strength for grasping the tissue after the tissue is closed, so that a mucosal layer of the tissue is pierced to prevent the tissue from slipping off.

Figure 7C:
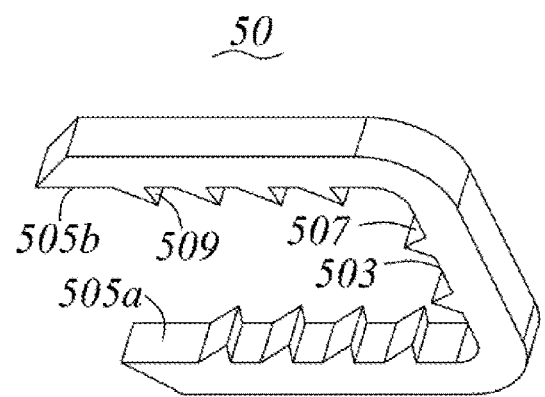
FIG. 7c is a schematically perspective view of a closure staple according to a third embodiment of the present invention.

As shown in FIG. 7c, in a third embodiment of the present invention, each of the side walls 505a and 505b of the closure staple 50 is further provided with at least one barb 509 whose end point faces to the bottom 503 of the closure staple 50. It can be understood that in the present embodiment, the bottom 503 of the closure staple 50 may also be provided with at least one spike-shaped portion 507 (FIG. 7c illustrates a case where two spike-shaped portions are provided). Of course, in the present embodiment, no spike-shaped portion 507 may be arranged on the bottom 503 of the closure staple 50.

The closure staple 50 may be a metal staple or may be made of other materials having a certain strength and elasticity.

Figure 8:
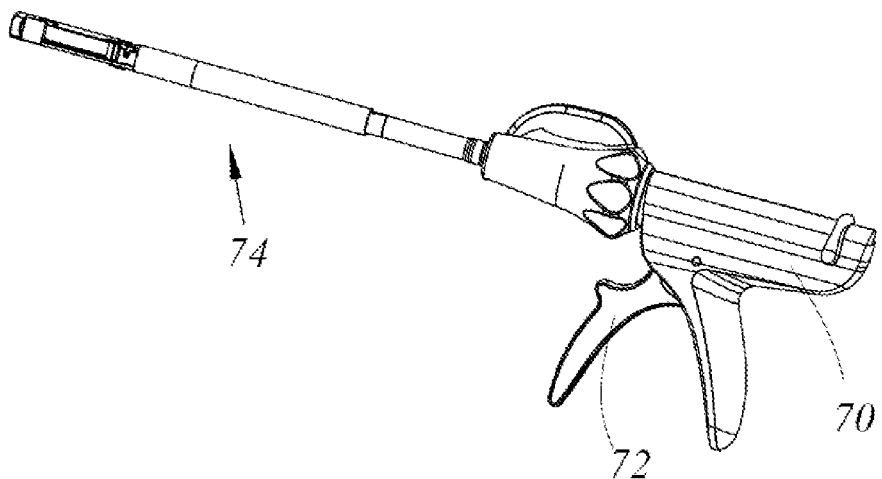
FIG. 8 is a schematically perspective view of a medical instrument according to a fourth embodiment of the present invention.
Figure 9:
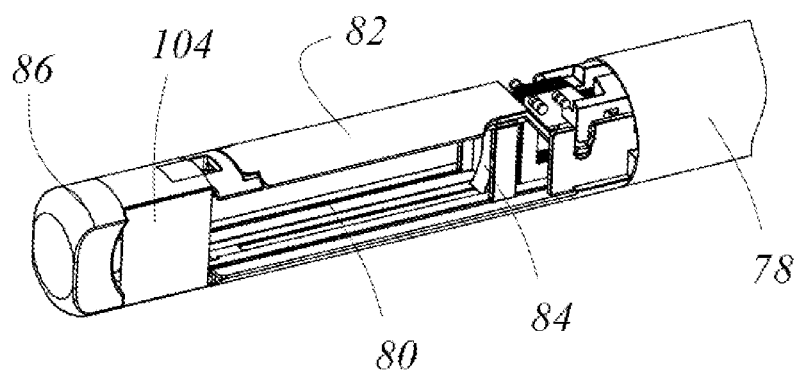
FIG. 9 is a schematically perspective view of a tissue closure assembly in which a pressure plate is at a closure position according to the fourth embodiment of the present invention.

As shown in FIG. 8, the present invention discloses a fourth embodiment of a medical instrument. The medical instrument may be used in a digestive tract anastomosis surgery. The medical instrument comprises an instrument body 70, an firing handle 72 pivotally connected to the instrument body 70, and a tissue closure device 74 detachably connected to the instrument body 70. In general, the tissue closure device 74 is arranged at the distal end of the instrument body 70.

Similarly, the structure of the instrument body 70 may be the same as that of an instrument body of an existing linear or arcuate stapler, or may be designed separately. It can be understood that the structure of the instrument body 70 is only required to cooperate with the tissue closure device 74 to work. In the following description, the structure of the instrument body of the existing linear or arcuate stapler will serve as that of the instrument body 70 in the present embodiment to illustrate.

In addition, the present invention further discloses an embodiment of a tissue closure assembly. The tissue closure assembly comprises a tissue closure device 74 and a closure staple 76 capable of being assembled to the tissue closure device 74. Structures and use manners of both the tissue closure device 74 and the closure staple 76 will be described in detail below.

As shown in FIGS. 9, 10, 11 and 12, the tissue closure device 74 comprises a connection portion 78, a base 80, a pressure plate 82 cooperating with the base 80, a staple pushing sheet 84, and a staple accommodating portion 86.

The connection portion 78 is configured to connect the instrument body 70. The base 80 is arranged at the distal end of the connection portion 78, and is integrally formed with the connection portion 78.

In the preferred embodiment, the pressure plate 82 may be pivotably connected to the base 80 to enable the pressure plate 82 to rotate relative to the base 80. The staple accommodating portion 86 is arranged at the distal end of the base 80.

Further, the staple accommodating portion 86 and the base 80 are integrally formed; and the inner bottom wall of the staple accommodating portion 86 smoothly transits to the inner bottom wall of the base 80 through an arcuate or inclined surface.

In the present embodiment, the cross section of the staple accommodating portion 86 is U-shaped.

Further, the pressure plate 82 comprises an open position and a closure position. For example, the open and closure positions are two extreme positions or positions close to the extreme positions (caused by an error in the mechanical cooperation process) when the pressure plate 82 pivotally rotates. When the pressure plate 82 is at the closure position, the pressure plate 82 and the base 80 cooperate to form a first accommodating space 90 for accommodating part of a tubular tissue. The first accommodating space 90 is a cavity with two open ends. During surgery, a tubular tissue (e.g., an intestinal tract, etc.) may be received at the open position. At the closure position, part of the tubular tissue is located between the pressure plate 82 and the base 80.

In an embodiment of the present invention, the staple accommodating portion 86 forms a second accommodating space 92 communicated with the first accommodating space 90. That is, the opening of the second accommodating space 92 faces the staple pushing sheet 84. The height of the second accommodating space 92 is bigger than the height of the first accommodating space 90. That is, the distance from the base 80 to the pressure plate 82 is less than the aperture of the opening of the second accommodating space 92.

Further, the staple accommodating portion 86 may also be configured to accommodate at least one closure staple 76. The staple pushing sheet 84 and the staple accommodating portion 86 are configured to cooperatively drive the closure staple 76 located in the staple accommodating portion 86 to form.

In addition, the tissue closure assembly further comprises a cutting knife 91 assembled to the tissue closure device 74. The staple accommodating portion 86 is arranged at the distal end of the base 80 and is configured to place the cutting knife 91.

Figure 11:
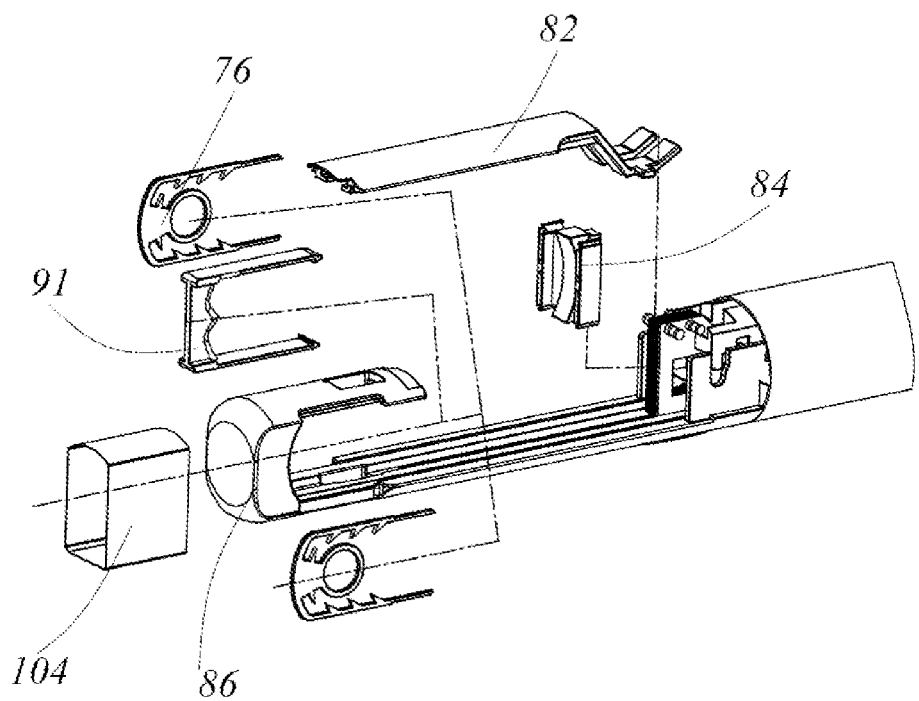
FIG. 11 is an exploded perspective view of the tissue closure assembly according to the fourth embodiment of the present invention.

As shown in FIG. 11, in the present preferred embodiment, two closure staples 76 can be accommodated into the staple accommodating portion 86 once. Particularly, the two closure staples 76 are located at the two sides of the cutting knife 91, respectively. In this way, two bundled pouches of the tissue may be formed at the same time. Of course, it is also feasible that only one or more than two closure staples 76 can be accommodated into the staple accommodating portion 86 once.

Correspondingly, the second accommodating space 92 comprises at least one staple accommodating groove (not shown). The staple accommodating groove may be formed by the inner wall of the staple accommodating portion 86, or may be arranged on the inner wall of the staple accommodating portion 86.

Further, the tissue closure device 74 further comprises a staple case communicated with the staple accommodating groove of the staple accommodating portion 86. A staple pushing structure (for example, a return spring) is arranged in the staple case to load a closure staple 76 in the staple case into the staple accommodating groove. Therefore, once there is no closure staple 76 in the staple accommodating groove (for example, after the firing is completed and the tissue is taken out), another closure staple 76 will be automatically loaded into the staple accommodating groove.

Further, the staple case is arranged in the staple accommodating portion 86. For example, the staple case may be arranged in a body of the staple accommodating portion 86 opposite to the opening of the staple accommodating portion 86. Of course, the staple case may be movably connected to the staple accommodating portion 86 to facilitate the replacement and loading of the closure staple 76.

In addition, a protective sheet 104 (see FIG. 12) is also arranged at the distal end of the base 80, so that contact of the closure staple 76 and the cutting knife 91 can be avoided when a tissue is received and a doctor adjusts the position, thereby preventing harm. At first, the protective sheet 104 covers a notch at the distal end; and then, the protective sheet 104 is tightened and compressed to the distal end close to the staple accommodating portion 86 along the compression of the tissue during the process that the staple pushing sheet 84 moves from the original position to the staple closure position. In the preferred embodiment, the material of the protective sheet 104 is an elastic film.

Figure 13A:
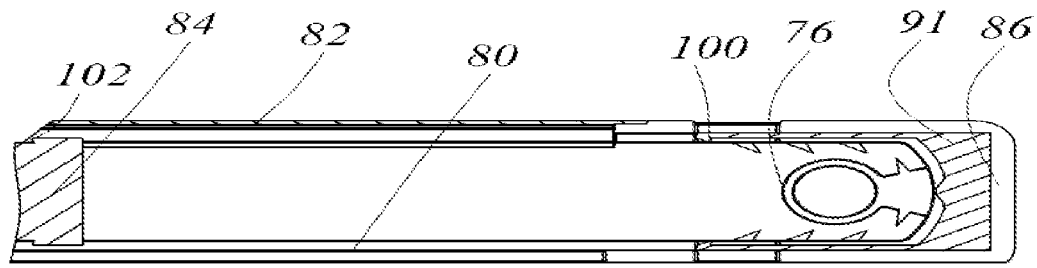
FIG. 13a is a sectional view of the tissue closure assembly in which a staple pushing sheet is at an original position according to the fourth embodiment of the present invention.

Moreover, the specific shape of the staple pushing sheet 84 is not limited as long as it can cooperate with the staple accommodating portion 86 to drive the closure staple 76 to form so as to complete the closure of the tissue. In an embodiment, the distal end surface of the staple pushing sheet 84 is a planar deforming groove, so that when the staple pushing sheet 84 moves from the original position to the staple closure position (as shown in FIG. 13c), the tubular tissue arranged in the first accommodating space 90 is gradually gathered towards the second accommodating space 92 and is totally accommodated in the second accommodating space 92 finally. It can be understood that, during the surgery, when the staple pushing sheet 84 is at the original position, no matter whether the tubular tissue is accommodated in both the first accommodating space 90 and the second accommodating space 92 or is only accommodated in the first accommodating space 90, the tubular tissue in the first accommodating space 90 is pushed into the second accommodating space 92 during the process that the staple pushing sheet 84 moves from the original position to the staple closure position, so that when the staple pushing sheet 84 reaches the staple closure position, the tubular tissue gathered in the second accommodating space 92 is bundled into a pouch.

In another embodiment, the distal end surface of the staple pushing sheet 84 may be an arcuate deforming groove. Thus, during the process that the staple pushing sheet 84 moves from the original position to the staple closure position, the arcuate end of the deforming groove is in contact with the closure staple 76 first, and applies a pressure to the open end of the closure staple 76 during the continuous movement of the staple pushing sheet 84 to bend the open end of the closure staple 76, so as to bundle the gathered tubular tissue into a pouch. The deforming groove may form a third accommodating space 94 to accommodate part of the tubular structure. When the pushing staple piece 84 reaches the staple closure position, the third accommodating space 94 may seal the second accommodating space 92 in the axial direction of the tissue closure device, so that the size of the accommodating spaces of the tubular tissue is increased. It can be understood that the third accommodating space 94 is actually a part of the first accommodating space 90.

It can be understood that if the deforming groove of the staple pushing sheet 84 has different shapes, the shape of a formed staple also changes accordingly. For example, the shape of the staple after closure may be "B"-shaped approximately.

Further, the staple pushing sheet 84 comprises an original position and a staple closure position. The original position is located at the proximal end of the staple closure position and the first accommodating space 90 (as shown in FIG. 13a). In general, when being at the original position, the staple pushing sheet 84 does not act on the proximal end of the pressure plate 82. Here, the pressure plate 82 is opened to receive a tubular tissue to be operated. When moving from the original position to the staple closure position, the staple pushing sheet 84 acts on the proximal end of the pressure plate 82 and is close to the base 80, so as to reach the closure position of the pressure plate 82. The working principle of the staple pushing sheet may refer to a cooperation structure of an I-shaped knife, a staple cartridge and a staple anvil of a linear or arcuate stapler, which will not be repeated herein.

Further, the staple pushing sheet 84 further comprises a pulling-back position. Particularly, the original position is located at the proximal end of the staple closure position and the first accommodating space (see FIG. 13a). The pulling-back position is located between the original position and the staple closure position (See FIG. 13d). The pulling-back position in the present invention is the position during the movement from the staple closure position to the original position, namely, the position during the movement from the distal end to the proximal end. Particularly, the pulling-back position is the position between the original position and the closure position during the movement from the distal end to the proximal end after the closure staple reaches the closure position.

Figure 13B:
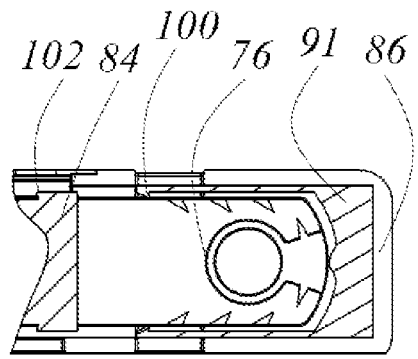
FIG. 13b is a sectional view of the tissue closure assembly in which the staple pushing sheet moves from the original position to a staple closure position according to the fourth embodiment of the present invention.
Figure 13C:
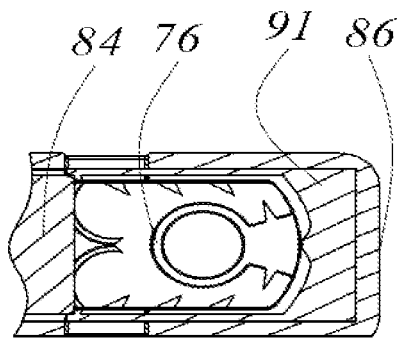
FIG. 13c is a sectional view of the tissue closure assembly in which the staple pushing sheet reaches the staple closure position according to the fourth embodiment of the present invention.
Figure 13D:
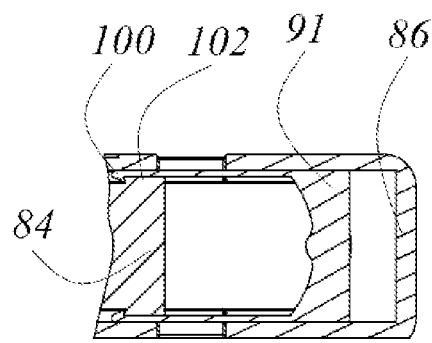
FIG. 13d is a sectional view of the tissue closure assembly in which the staple pushing sheet moves from the staple closure position to a pulling-back position according to the fourth embodiment of the present invention.

Further referring to FIGS. 13c and 13d, when the staple pushing sheet 84 moves from the staple closure position to the pulling-back position, the staple pushing sheet 84 cooperates with the cutting knife 91 to drive the cutting knife 91 to move from the distal end of the base 80 to the proximal end to cut off the tissue. When the staple pushing sheet 84 reaches the pulling-back position, the cutting knife 91 is cutting the tissue or has cut off the tissue; and finally, the staple pushing sheet returns to the original position to open the pressure plate 82.

Further, the cutting knife 91 selectively disengages from or engages with the staple pushing sheet 84. As shown in FIG. 13a, at an original position, the staple pushing sheet 84 disengages from the cutting knife 91; and at a staple closure position, the staple pushing sheet 84 engages with the cutting knife 91. Particularly, at the original position, the staple pushing sheet 84 is located at the proximal end of the base 80, and the cutting knife 91 is located at the distal end of the base 80 and is accommodated in the staple accommodating portion 86. At this time, the cutting knife 91 disengages from the staple pushing sheet 84. At the staple closure position, the staple pushing sheet 84 moves to the distal end of the base 80. At this time, the staple pushing sheet 84 pushes the closure staple to be closed and formed, and engages with the cutting knife 91 accommodated in the staple accommodating portion 86. Then, the staple pushing sheet 84 moves from the staple closure position to the pulling-back position. At this time, the staple pushing sheet 84 drives the cutting knife 91 to move from the distal end of the base 80 to the proximal end to cut off the tissue. Particularly, the cutting knife 91 is provided with a cooperation portion 100. The staple pushing sheet 84 is provided with an engagement portion 102 capable of selectively engaging with or disengaging from the cooperation portion 100. When the staple pushing sheet 84 moves from the staple closure position to the pulling-back position, the cooperation portion 100 engages with the engagement portion 102 to enable the staple pushing sheet 84 to drive the cutting knife 91 to move from the distal end of the base 80 to the proximal end to cut off the tissue. When the staple pushing sheet 84 moves from the original position to the staple closure position, the cooperation portion 100 disengages from the engagement portion 102. Further, the cooperation portion 100 is a clasp; and the cooperation portion 102 is a protrusion.

In the preferred embodiment, at the original position, the staple pushing sheet 84 disengages from the cutting knife 91. At this time, an operation only for closing and forming the staple to form a pouch is actuated. After the closure of the closure staple 76 is actuated and the pouch is formed, the staple pushing sheet 84 and the cutting knife 91 cooperate to drive the cutting knife 91 to move from the distal end of the base 80 to the proximal end to cut the tissue formed as the pouch. Moreover, during cutting, the pouch remains immobile under the action of the closure device. Through this manner, namely first performing closing and then cutting, on one hand, the safety of the surgery is ensured, and a risk of cutting the tissue when the pouch is not formed is avoided. On the other hand, the closure formation of the staple and cutting are separated, an firing force of the instrument is also reduced, and the reliability of the instrument is improved. The tissue is cut under a pouch fixation state, so that remaining a lip according to a design specification may be ensured. In addition, the operation is simpler, the use is more convenient, and the surgery cost is further reduced.

Figure 14:
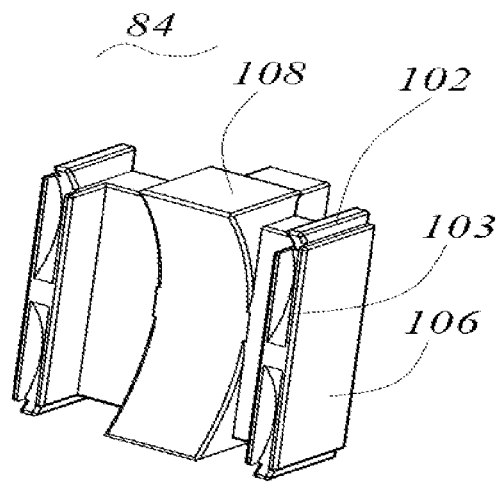
FIG. 14 is a schematically perspective view of the staple pushing sheet according to the fourth embodiment of the present invention.

As shown in FIG. 14, in the preferred embodiment, the staple pushing sheet 84 is provided with a staple deforming groove 103. Side walls 106 for compressing the tissue are arranged at the two sides of the staple deforming groove 103, respectively, and are higher than the staple deforming groove 103. That is, the side walls are located at the side closer to the staple deforming groove. In other words, the side walls 106 are located at the distal end of the staple deforming groove 103. The side walls 106 are thin walls. In this way, the tissue is first compressed, and then the closure staple 76 is formed, so that it is ensured that the tissue is completely received in the closure staple 76. Meanwhile, the thin side walls 106 can ensure adequate compression on the tissue and can acquire a greater compression ratio. The engagement portion 102 cooperatively connecting with the cutting knife 91 (see FIG. 13d) is arranged on the side walls 106.

Further, a middle wall 108 is arranged between the two side walls 106 of the staple pushing sheet 84, and is lower than the side walls 106. That is, the middle wall 108 is located at the proximal end of the staple deforming groove 103. In this way, the middle wall 108 is lower than a space portion of the side walls 106. That is, a portion between the two side walls is hollowed to form an escape space for the tissue when it is compressed, so that a contact area of the middle wall 108 and the tissue is reduced, and the side walls 106 can further compress the tissue, thereby reducing an firing force. Particularly, the middle wall 108 is provided with an arcuate recess portion so as to reduce the contact area of the middle wall and the tissue.

Further referring to FIGS. 13b and 13c, in the present preferred embodiment, during the process that the staple pushing sheet 84 moves from the original position to the staple closure position, the staple pushing sheet 84 and the staple accommodating portion 86 drive the closure staple 76 to form. At this time, the cutting knife 91 is fixed relative to the staple accommodating portion 86, so as not to cut the tissue. When the staple pushing sheet 84 reaches the staple closure position, the closure staple 76 is closed to bundle the tissue into a pouch; and meanwhile, the staple pushing sheet 84 engages with the cutting knife 91. Referring to FIG. 13d, when the staple pushing sheet 84 moves from the staple closure position to the pulling-back position, namely, from the distal end to the proximal end, the staple pushing sheet 84 engages with the cutting knife 91 and drives the cutting knife 91 to move so as to cut the tissue formed as the pouch. At this time, the closure staple 76 remains stationary with respect to the staple accommodating portion 86. In this way, the tissue is cut off during a return process of the staple pushing sheet 84, and the operation is very simple. In addition, at the original position, the cutting knife 91 is located at the distal end of the base 80. After the closure staple 76 is closed to bundle the tissue into the pouch, the cutting knife 91 starts to move under the driving of the staple pushing sheet 84 to cut the bundled tissue, so that the cutting knife 91 does not harm the tissue when the closure staple 76 is not formed.

Particularly, the staple accommodating portion 86 (see FIG. 13d) is provided with a step (not shown) so as to limit the movement of the closure staple 76 towards the proximal end direction. In this way, cutting is performed while keeping the pouch stationary, so that the cut lip is cut according to a plan, thereby avoiding damage to the pouch and failure of the surgery caused by the too narrow lip. Meanwhile, the uniformity of the lip width after cutting is ensured. Preferably, the distance from the cutting knife 91 to the pouch is 3-5 mm. That is, the width of the lip is 3-5 mm. Therefore, the reliability of the pouch is ensured, and the size of the pouch is not too large, so that the pouch can easily enter a tubular stapler in a subsequent surgery process to reconstruct the tissue.

Figure 15:
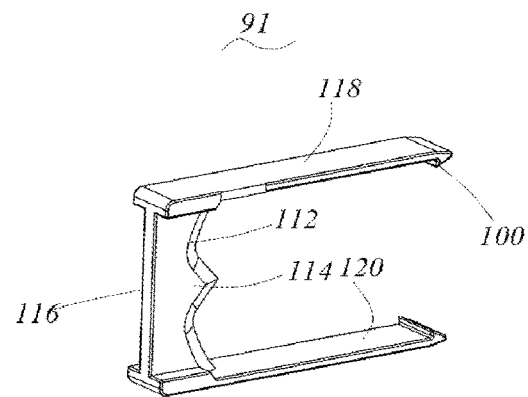
FIG. 15 is a schematically perspective view of a cutting knife according to the fourth embodiment of the present invention.

As shown in FIG. 15, the cutting knife 91 comprises a cutting portion 116 for cutting off a tissue, as well as a first connection portion 118 and a second connection portion 120 which are located at the two opposite sides of the cutting portion 116 respectively and are connected to the cutting portion 116. The cutting portion 116 is provided with a halberd blade 114 for cutting off the bottom wall of the tissue. The halberd blade 114 has a tip portion. Further, the cutting portion 116 is further provided with an oblique blade 112 for slidably cutting off the side walls of the tissue. Particularly, there are two oblique blades 112 distributed at the two sides of the halberd blade 114. The halberd blade 114 is configured to cut the bottom wall of the pouch tissue into two sections from the center, so as to further improve the amputation performance. Particularly, the halberd blade 114 has the tip portion to puncture the tissue, so that the amputation of the tissue is ensured.

In the preferred embodiment, the oblique blades 112 extend along a curve, and are smoothly connected with the halberd blade 114. The oblique blades 112 and the halberd blade 114 form an approximately "W"-shaped knife. That is, the middle of the "W"-shaped knife is the halberd blade, and the two sides of the "W"-shaped knife are the oblique blades. In addition, the oblique blades 112 and the halberd blade 114 form a recess portion, so that the cutting knife 91 can be in contact with the bundled pouch conveniently in the moving process to cut off the tissue. Preferably, during the movement of the cutting knife 91, the halberd blade 114 is in contact with the bundled pouch first to amputate it from the center. Then, the oblique blades 112 are in contact with the bundled pouch and cut it. Thus, the oblique blades 112 and the halberd blade 114 cut off the tissue.

In the present preferred embodiment, the first connection portion 118 and the second connection portion 120 may selectively engage with or disengage from the staple pushing sheet 84. That is, the cooperation portion 100 is arranged on the first connection portion 118 and the second connection portion 120. Particularly, the cutting portion 116 and the cooperation portion 100 are located at the two opposite ends of the first connection portion 118 and the second connection portion 120, respectively. In addition, one oblique blade 112 and the first connection portion 118 form an obtuse angle, so do the other oblique blade 112 and the second connection portion 120.

In the preferred embodiment, each of the first connection portion 118 and the second connection portion 120 may be provided with a clamping groove (not shown) in which the cutting portion 116 is fixed. In addition, the cutting portion 116, the first connection portion 118 and the second connection portion 120 may be welded together. Of course, the cutting portion 116, the first connection portion 118 and the second connection portion 120 may also be integrally formed.

Figure 16A:
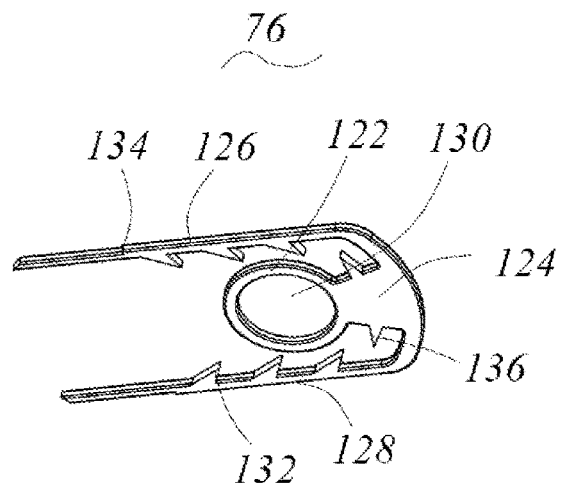
FIG. 16a is a schematically perspective view of a closure staple according to the fourth embodiment of the present invention.
Figure 16B:
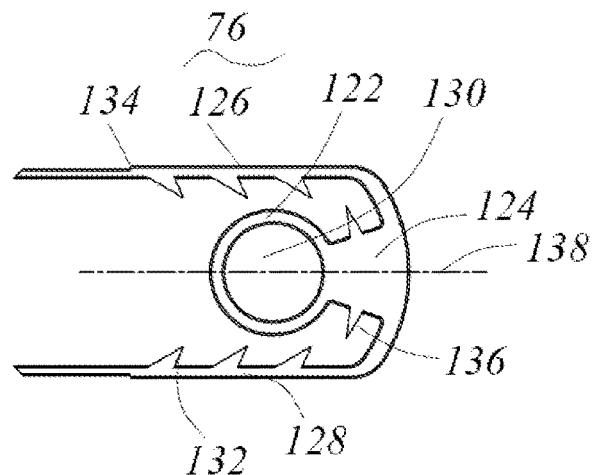
Figure 16C:
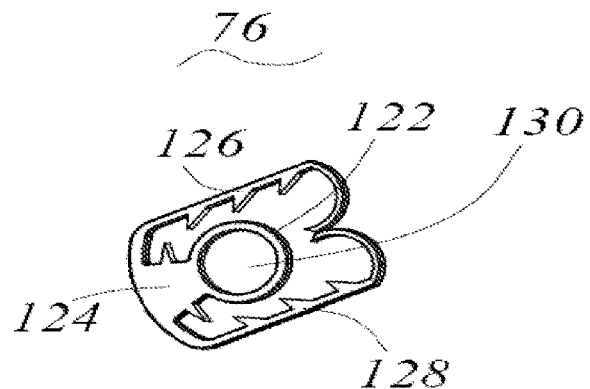
FIG. 16c is a schematically perspective view of the closure staple shown in FIG. 16a after being bent.

As shown in FIGS. 16a, 16b and 16c, the present preferred embodiment further discloses a closure staple 76 for a tissue closure assembly 14. The tissue closure assembly comprises a tissue closure device. The closure staple 76 may be assembled to the tissue closure device. The tissue closure device can be operated to bend and form the closure staple 76. In addition, the design of the tissue closure device only needs to meet the requirement that once an firing handle 72 is operated, the tissue closure device is driven to act to drive the closure staple 76 to be bent and formed. The details will not be repeated herein. The following is a detailed description on the closure staple 76.

The closure staple 76 comprises a base portion 122, a connection portion 124 connected with the base portion 122, as well as a first side portion 126 and a second side portion 128 which are connected with the connection portion 124. The first side portion 126 and the second side portion 128 are located at the two sides of the connection portion 124, respectively. An opening is formed between the first side portion 126 and the second side portion 128. The base portion 122 constitutes a closed channel 130 allowing an instrument to pass through.

In the present preferred embodiment, as the base portion 122 of the closure staple 76 constitutes the closed channel 130 allowing an instrument to pass through, when introducing the instrument such as a lead screw, the instrument can be inserted from the closed channel 130, without being in contact with the pouch. Thus, no external force will be applied to the pouch, and the pouch will not slip off due to the force. Therefore, the closure staple 76 not only facilitates the insertion of the instrument, but also prevents the pouch from slipping off due to the force when the instrument is inserted.

A thorn portion 132 is arranged at the side of each of the first side portion 126 and the second side portion 128 close to the base portion 122. In this way, the thorn portions 132 can pierce through the tissue to grasp the mucosal layer of the tissue, so as to prevent the tissue from slipping off. Preferably, the thorn portions 132 extend in the direction towards the connection portion 124. Of course, the thorn portions 132 may also be designed to extend in other directions.

Further, there are multiple thorn portions 132 on each of the first side portion 126 and the second side portion 128. Particularly, in the preferred embodiment, three thorn portions 132 are arranged on each of the first side portion 126 and the second side portion 128; and the thorn portions 132 on the first side portion 126 and the second side portion 128 are symmetrical. Of course, other numbers of thorn portions 132 may also be arranged on the first side portion 126 and the second side portion 128. Likewise, the thorn portions 132 on the first side portion 126 and the second side portion 128 may also be asymmetrical.

In addition, a step 134 is arranged on each of the first side portion 126 and the second side portion 128. The step 134 and the thorn portion 132 are located at the two opposite sides of each of the first side portion 126 and the second side portion 128, respectively. The step 134 facilitates the bending and formation of the closure staple 76 while cooperating with the step (not shown) of the staple accommodating portion 86 to prevent the formed pouch from moving during the pull back process of the cutting knife 91.

In the present preferred embodiment, the free end of each of the first side portion 126 and the second side portion 128 is arranged as a chamfer, so that the closure staple 76 is closed and formed in the staple deforming groove 103.

In the closure process, when the staple pushing sheet 84 is at the original position, the free end of the closure staple 76 is opposite to the staple pushing sheet 84. Particularly, the free ends of the first side portion 126 and the second side portion 128 are opposite to the staple pushing sheet 84. When the staple pushing sheet 84 is at the staple closure position, the free end of the closure staple 76 contains the gathered tubular tissue and is bent and formed under the action of the staple pushing sheet 84. Particularly, the free end of each of the first side portion 126 and the second side portion 128 contains the gathered tubular tissue and is bent and formed under the action of the staple pushing sheet 84, so as to form a closure shape shown in FIG. 9c.

Preferably, the first side portion 126 is parallel to the second side portion 128. Of course, the first side portion 126 and the second side portion 128 may also be unparallel and form a small angle.

In the preferred embodiment, the closed channel 130 is circular. The closed channel 130 is generally configured to allow an instrument such as a lead screw of a circular stapler to penetrate through. Of course, the closed channel 130 can also be designed into other shapes.

In addition, it can be understood that in the preferred embodiment, at least one spike-shaped portion 136 may also be arranged on the connection portion 124. In this way, after the tissue is closed, the spike-shaped portion 136 pierces through the tissue to increase the strength for grasping the tissue, so that the tissue is prevented from slipping off due to a force. Of course, no spike-shaped portion 136 may be arranged on the connection portion 124 of the closure staple 76 in the present embodiment.

Further, two spike-shaped portions 136 are arranged on the connection portion 124, and are configured to grasp the tissue to prevent the tissue from slipping. Particularly, the centers of both the connection portion 124 and the closed channel 130 define a center line 138. The two spike-shaped portions 136 on the connection portion 124 are symmetrical with respect to the center line 138. Of course, the two spike-shaped 136 on the connection portion 124 may also be asymmetrical with respect to the center line 138.

Figure 12:
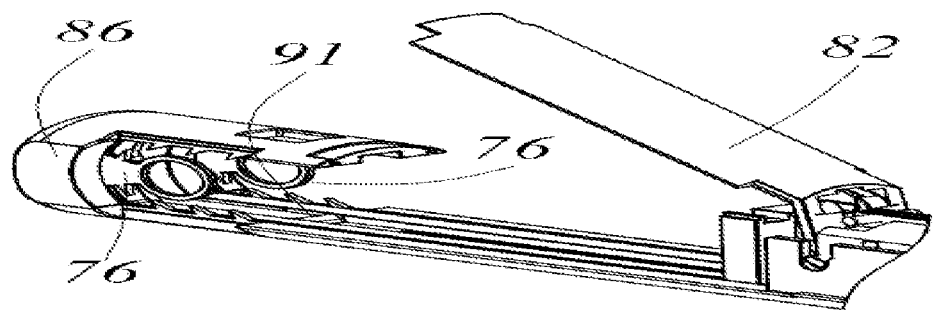
FIG. 12 is another schematically perspective view of the tissue closure assembly in which the pressure plate is at an open position according to the fourth embodiment of the present invention.

In addition, when the pressure plate 82 (see FIG. 8) is in the closure process and the staple pushing sheet 84 (see FIG. 8) is at the original position, the first side portion 126 and the second side portion 128 of the closure staple 76 are opposite to the staple pushing sheet 84. Referring to FIG. 12, when the staple pushing sheet 84 is at the staple closure position, the first side portion 126 and the second side portion 128 of the closure staple 76 are bent and formed under the action of the staple pushing sheet 84.

Figure 10:
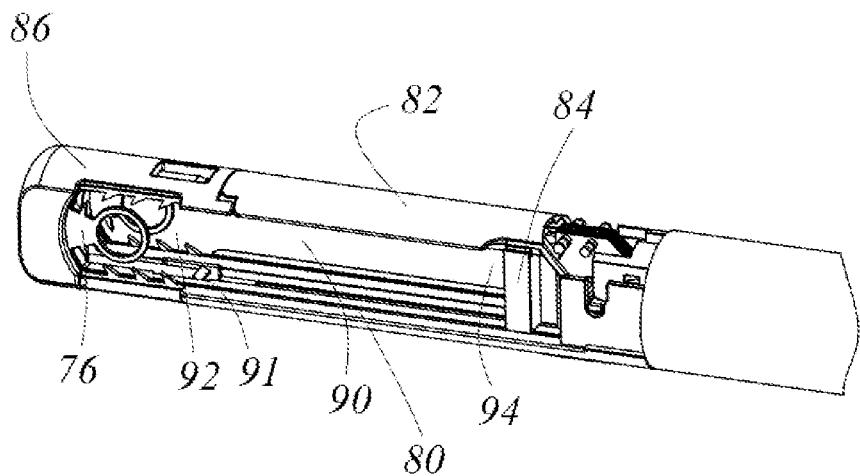
FIG. 10 is another schematically perspective view of a tissue closure assembly in which a protective sheet is removed and the pressure plate is at a closure position according to the fourth embodiment of the present invention.

Further referring to FIG. 10, when the tissue closure device is operated to apply pressure to the free end of the closure staple 76 to bend the same, the free ends of both the first side portion 126 and the second side portion 128 of the closure staple 76 are bent inwards from their respective steps 134 so as to bundle the gathered tubular tissue into a pouch. Of course, if no step is arranged on the free ends of the first side portion 126 and the second side portion 128 of the closure staple 76, the closure staple 76 will be bent and formed. Of course, the deforming groove 43 (see FIG. 14) of the staple pushing sheet 84 of the tissue closure device can also be set to different shapes as required, and accordingly, the shape of the formed closure staple 76 also changes. For example, the shape of the staple after closure may be "B"-shaped approximately. It can be understood that the shape is not limited as long as the gathered tubular tissue can be bundled into the pouch after closure.

Likewise, the closure staple 76 may be a metal staple or may be made of other materials having a certain strength and elasticity.

Particularly, in the preferred embodiment, when the tissue closure device is operated to enable the staple pushing sheet 84 to move from the original position to the staple closure position, the staple deforming groove 103 of the staple pushing sheet 84 is abutted against the first side portion 126 and the second side portion 128 of the closure staple 76, so as to bend and form the first side portion 126 and the second side portion 128. When the staple pushing sheet 84 moves to the staple closure position, the closure staple 76 is bent and formed so as to bundle the tissue into a pouch. Meanwhile, the engagement portion 102 of the staple pushing sheet 84 engages with the cooperation portion 100 of the cutting knife 91. When the staple pushing sheet 84 moves from the staple closure position to the pull back position, the staple pushing sheet 84 drives the cutting knife 91 to move from the distal end of the base 80 to the proximal end, thereby cutting off the tissue formed as the pouch.

In summary, through the tissue closure device, the tissue closure assembly and the medical instrument provided by the present preferred embodiments, the bundled pouch with a gathered center may be formed, so that risks of "dog ears" and stoma fistula arising from subsequent anastomosis through a circular stapler are reduced. In addition, the tissue can be closed through only one operation, so that the use is more convenient, and the surgery cost is reduced. Moreover, the tissue is cut after being closed, so that the cutting knife 91 does not harm the tissue when the closure staple 76 is not formed; and meanwhile, the uniformity of the lip width after cutting is ensured.

Figure 17A:
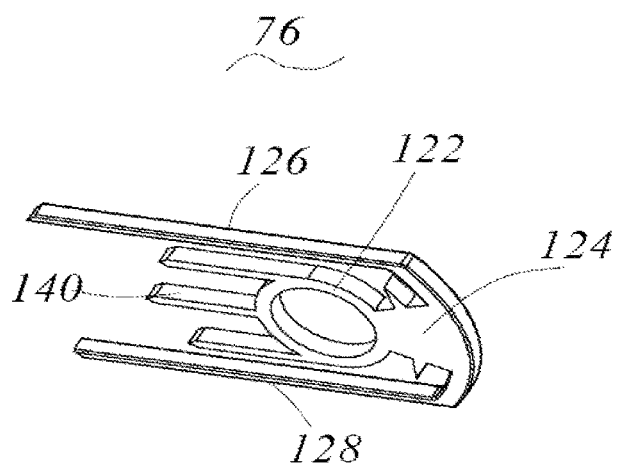
FIG. 17a is a schematically perspective view of a closure staple according to a fifth embodiment of the present invention.
Figure 17B:
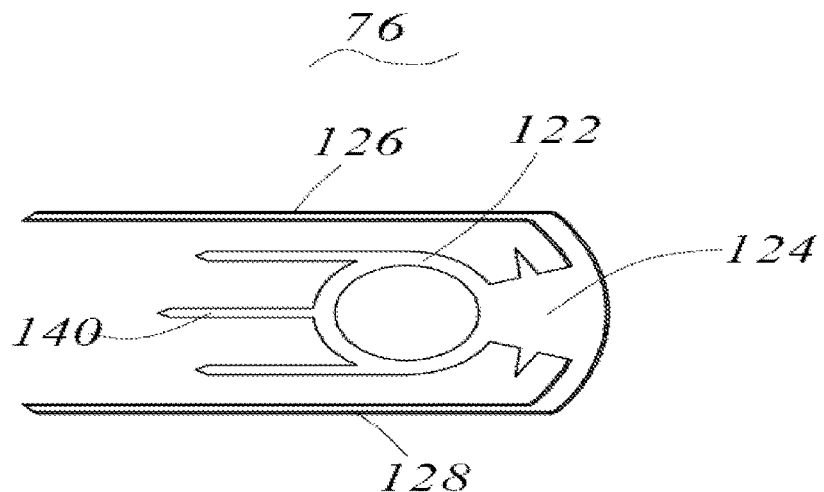

As shown in FIGS. 17*a* and 17*b*, the closure staple 76 provided by the fifth preferred embodiment of the present invention differs from that provided by the fourth embodiment in that there is no thorn arranged on the first side portion 126 or the second side portion 128; and an extension rod 140 is arranged on the base portion 122. The extension rod 140 and the connection portion 124 are located at the two opposite sides of the base portion 122. Particularly, the extension rod 140 is provided with a spike-shaped end.

In the preferred embodiment, there are three extension rods 140. An extension line of the first extension rod 140 passes through the center of the base portion 122, and the other two extension rods 140 are symmetrical with respect to the first extension rod 140. Of course, other numbers of extension rods may also be provided.

Figure 18A:
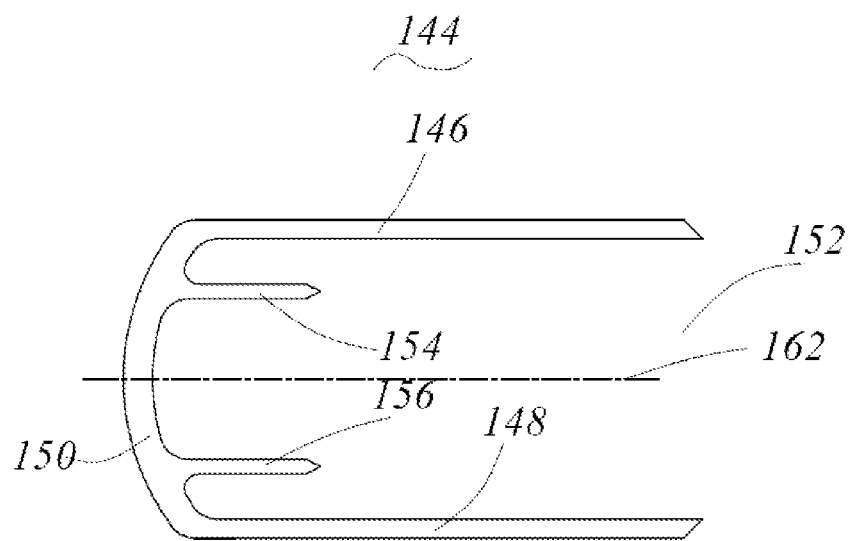
FIG. 18a is a front view of a closure staple according to a sixth embodiment of the present invention.
Figure 18B:
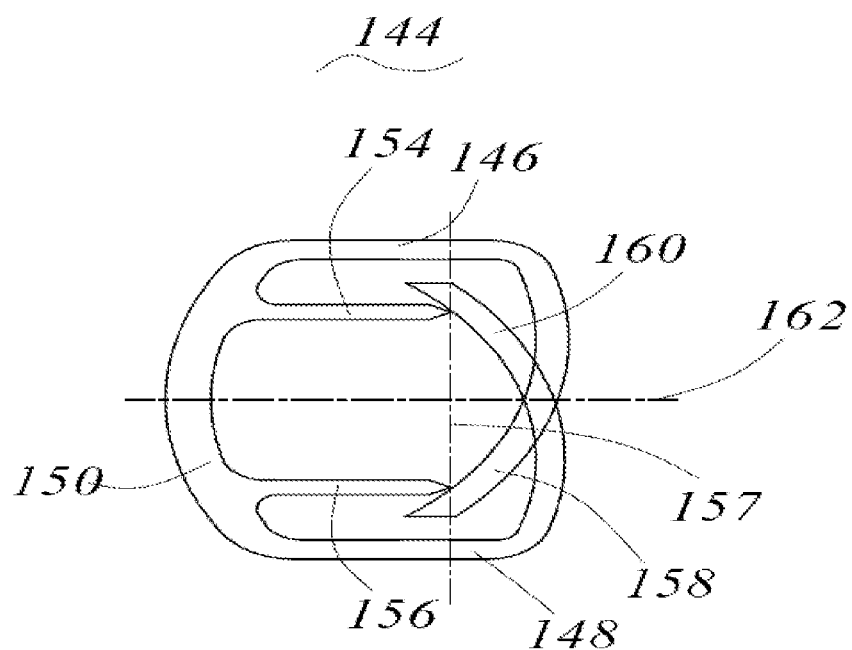
FIG. 18b is a front view of the closure staple shown in FIG. 18a after being bent.

As shown in FIGS. 18*a* and 18*b*, the closure staple 144 provided by the sixth preferred embodiment of the present invention differs from the closure staple 76 provided by the fourth embodiment in that there is no closed channel on the closure staple 144. The closure staple 144 comprises a first side portion 146, a second side portion 148 opposite to the first side portion 146, and a bottom 150 connected with the first side portion 146 and the second side portion 148. An opening portion 152 is formed between the first side portion 146 and the second side portion 148. The bottom 150 is opposite to the opening portion 152; and at least one thorn is arranged on the bottom 150.

In this way, the thorn on the bottom 150 will pierce through the mucosal layer of the tissue when the closure staple 144 is closed, so that the bundled pouch will be relatively firmer, and the pouch is unlikely to slip off when being pulled by an external force.

In addition, the free end of each of the first side portion 146 and the second side portion 148 is arranged as a chamfer, so that the closure staple 144 is closed and formed in the staple deforming groove 103.

In a preferred embodiment, particularly, a first thorn 154 and a second thorn 156 are arranged on the bottom 150 and are symmetrical. Of course, the first thorn 154 and the second thorn 156 may also be asymmetrical.

The first thorn 154 and the second thorn 156 have the same length. The first thorn 154 is taken as an example to describe in detail. The first end of the first thorn 154 is arranged on the bottom 150, and the second end thereof is a tail end. An opening portion 157 is defined through the tail end of the first thorn 154 and is perpendicular to the first thorn 154. After the closure staple 144 is bent and formed, bending portions of both the first side portion 146 and the second side portion 148 intersect with the opening portion 157. Thus, the bundled pouch is firmer and is prevented from slipping off when being pulled by an external force.

In addition, as the first thorn 154 and the second thorn 156 have the same length, the opening portion 157 also passes through the tail end of the second thorn 156. Of course, the lengths of the first thorn 154 and the second thorn 156 may also be different. Preferably, the lengths of the first thorn 154 and the second thorn 156 are within a size range of a space enclosed by the closed and formed closure staple 144 so as to avoid damage to the tissue.

Further, the first side portion 146 and the second side portion 148 define a first plane. After the closure staple 144 is bent and formed, a projection of a bending portion 158 of the first side portion 146 on the first plane intersects with that of a bending portion 160 of the second side portion 148 on the first plane. In addition, there is a center line 162 between the first side portion 146 and the second side portion 148. A cross point of the projections of both the bending portions 158 and 160 of the first side portion 146 and the second side portion 148 on the first plane is located on the center line 162, or of course, may not be located on the center line 162.

In addition, the projections of both the bending portions 158 and 160 of the first side portion 146 and the second side portion 148 on the first plane are located outside the first thorn 154 and the second thorn 156. That is, the projection of the bending portion 160 of the second side portion 148 is located between the first side portion 146 and the first thorn 154; and the projection of the bending portion 158 of the first side portion 146 is located between the second side portion 148 and the second thorn 156.

Figure 19A:
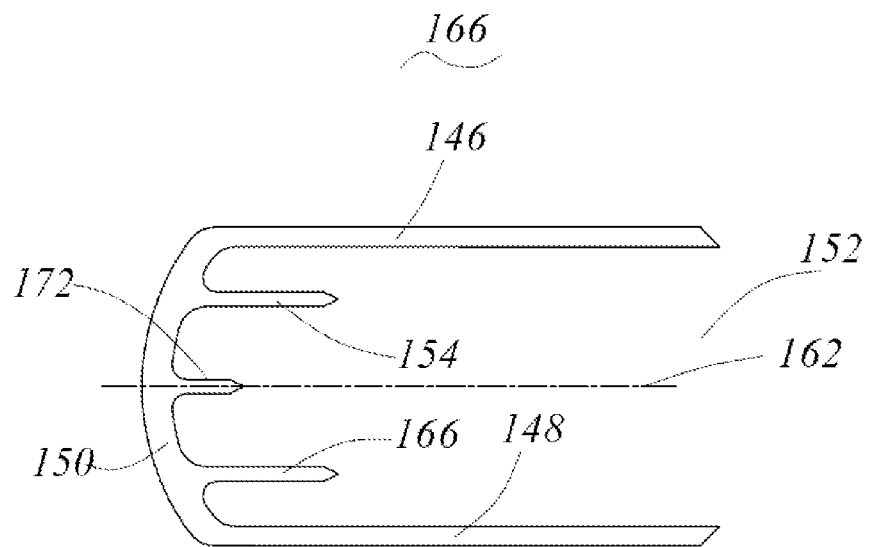
FIG. 19a is a front view of a closure staple according to a seventh embodiment of the present invention.
Figure 19B:
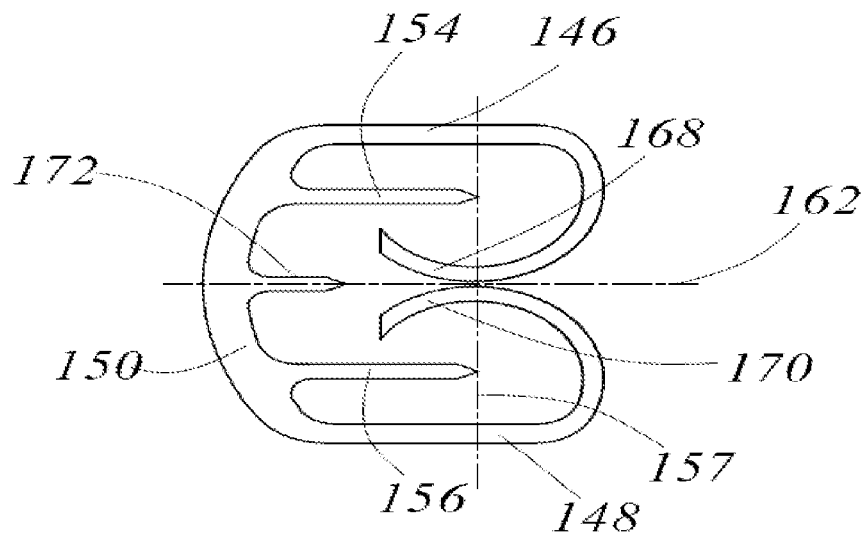
FIG. 19b is a front view of the closure staple shown in FIG. 19a after being bent.

As shown in FIGS. 19*a* and 19*b*, compared with the closure staple provided by the sixth preferred embodiment, the closure staple 106 provided by the seventh preferred embodiment of the present invention comprises a first side portion 146, a second side portion 148 opposite to the first side portion 146, and a bottom 150 connected with the first side portion 146 and the second side portion 148. An opening portion 152 is formed between the first side portion 146 and the second side portion 148. The bottom 150 is opposite to the opening portion 152; and at least one thorn is arranged on the bottom 150.

Likewise, when the closure staple 106 is bent and formed, both a bending portion 108 of the first side portion 146 and a bending portion 110 of the second side portion 148 intersect with the opening portion 157. In addition, as the first thorn 154 and the second thorn 156 have the same length, the opening portion 157 also passes through the tail end of the second thorn 156. Of course, the lengths of the first thorn 154 and the second thorn 156 may also be different. Preferably, the lengths of the first thorn 154 and the second thorn 156 are within a size range of a space enclosed by the closed and formed closure staple 144 so as to avoid damage to the tissue.

The first side portion 146 and the second side portion 148 define a first plane. Different from the third embodiment, in the present preferred embodiment, after the closure staple 106 is bent and formed, a projection of the bending portion 108 of the first side portion 146 on the first plane is away from that of the bending portion 110 of the second side portion 148 on the first plane.

Further, the projections of both the bending portions 108 and 110 of the first side portion 146 and the second side portion 148 on the first plane are located between the first thorn 154 and the second thorn 156.

A third thorn 112 is further arranged on the bottom 150, and the third thorn 112 coincides with the center line 162 between the first side portion 146 and the second side portion 148. Of course, the third thorn 112 may not coincide with the center line 162 of the first side portion 146 and the second side portion 148. Further, both the first thorn 154 and the second thorn 156 are longer than the third thorn 112.

Figure 20A:
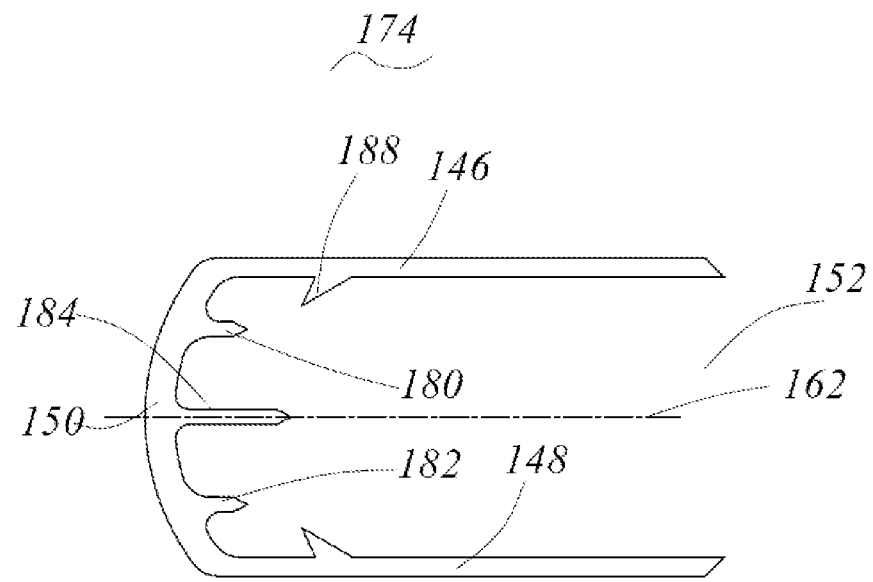
FIG. 20a is a front view of a closure staple according to an eighth embodiment of the present invention.
Figure 20B:
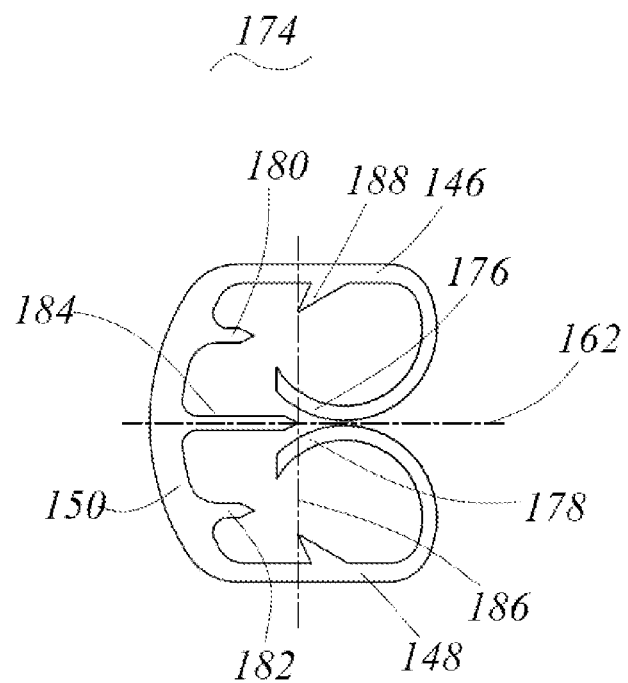
FIG. 20b is a front view of the closure staple shown in FIG. 20a after being bent.

As shown in FIGS. 20a and 20b, compared with the closure staple provided by the seventh preferred embodiment, in the closure staple provided by the eighth preferred embodiment of the present invention, the first side portion 146 and the second side portion 148 define a first plane. After the closure staple 174 is bent and formed, a projection of a bending portion 176 of the first side portion 146 on the first plane is away from that of a bending portion 178 of the second side portion 148 on the first plane.

The bottom 150 is provided with a first thorn 180 and a second thorn 182 symmetrical to the first thorn 180. Further, a third thorn 184 is also arranged on the bottom 150, and coincides with the center line 162 between the first side portion 146 and the second side portion 148. Of course, the third thorn 184 may not coincide with the center line 162 of the first side portion 146 and the second side portion 148. In the preferred embodiment, the third thorn 184 is longer than the first thorn 180 and the second thorn 182.

In addition, a perpendicular line 186 is defined through the tail end of the third thorn 184 and is perpendicular to the third thorn 184. After the closure staple 174 is bent and formed, the bending portion 176 of the first side portion 146 and the bending portion 178 of the second side portion 148 intersect with the perpendicular line 186. Thus, the bundled pouch is firmer and is prevented from slipping off when being pulled by an external force.

Further, a spike-shaped portion 188 is arranged on each of the first side portion 146 and the second side portion 148. Preferably, the spike-shaped portion 188 on the first side portion 146 is symmetrical to that on the second side portion 148. Particularly, the spike-shaped portions 188 extend in a direction towards the bottom 150.

In summary, through the tissue closure device, the tissue closure assembly and the medical instrument provided by the present invention, the bundled pouch with a gathered center may be formed, so that risks of "dog ears" and stoma fistula arising from subsequent anastomosis through a circular stapler are reduced. In addition, the tissue can be closed through only one operation, so that the use is more convenient, and the surgery cost is reduced.

It should be understood that although the description is described based on the embodiments, not every embodiment includes only one independent technical solution. This statement of the description is only for clarity. Those skilled in the art should treat the description as a whole, and technical solutions in all of the embodiments may also be properly combined to form other embodiments that will be understood by those skilled in the art.

The above detailed description only aims to specifically illustrate the available embodiments of the present invention, and is not intended to limit the protection scope of the present invention. Equivalent embodiments or modifications thereof made without departing from the spirit of the present invention shall fall within the protection scope of the present invention.

What is claimed is:

1. A tissue closure device, comprising: a base, a pressure plate cooperating with the base, and a staple pushing sheet, wherein the pressure plate is rotatable relatively to the base, and comprises an open position and a closure position; when the pressure plate is located at the closure position, the pressure plate cooperates with the base to form a first accommodating space for accommodating part of a tubular tissue;

the staple pushing sheet comprises an original position and a staple closure position; the original position is located at the proximal end of the staple closure position and the first accommodating space;

the tissue closure device further comprises a staple accommodating portion which is arranged at the distal end of the base and configured to accommodate at least one closure staple; and the staple pushing sheet and the staple accommodating portion are configured to cooperatively drive the closure staple located in the staple accommodating portion to deform;

the distal end surface of the staple pushing sheet is a deforming groove; during the process that the staple pushing sheet moves from the original position to the staple closure position, the deforming groove is in contact with the closure staple first, and applies a pressure to an open end of the closure staple in the continuous movement process of the staple pushing sheet so as to bend the open end of the closure staple.

2. The tissue closure device of claim 1, wherein a second accommodating space is formed in the staple accommodating portion, and is communicated with the first accommodating space, the height of the second accommodating space is bigger than the height of the first accommodating space.

3. The tissue closure device of claim 2, wherein the second accommodating space comprises at least one staple accommodating groove; and the staple accommodating groove is capable of accommodating at least part of the closure staple to fix a relative position between the closure staple and the staple accommodating portion.

4. The tissue closure device of claim 1, wherein during the process that the staple pushing sheet moves from the original position to the staple closure position, the tubular tissue in the first accommodating space is gradually gathered towards the second accommodating space and is totally accommodated in the second accommodating space finally.

5. The tissue closure device of claim 1, wherein the distal end surface of the staple pushing sheet is an arcuate deforming groove; and
when the staple pushing sheet reaches the staple closure position, the deforming groove forms a third accommodating space to accommodate part of the tubular tissue.

6. The tissue closure device of claim 1, wherein the tissue closure device further comprises a staple case communicating with the staple accommodating groove of the staple accommodating portion; and a staple pushing structure is arranged in the staple case to load the closure staple in the staple case into the staple accommodating groove.

7. The tissue closure device of claim 1, wherein the staple pushing sheet further comprises a pulling-back position between the original position and the staple closure position; the staple accommodating portion is further configured to place a cutting knife; and when the staple pushing sheet moves from the staple closure position to the pulling- back position, the staple pushing sheet cooperates with the cutting knife to drive the cutting knife to move from the distal end of the base to the proximal end so as to cut off the tissue.

8. The tissue closure device of claim 7, wherein when the staple pushing sheet drives the closure staple to be deformed from the proximal end to the distal end, the cutting knife is motionless relative to the staple accommodating portion, so as not to cut the tissue.

9. The tissue closure device of claim 8, wherein the staple pushing sheet is provided with a staple deforming groove for forming the closure staple, and side walls for compressing the tissue; and the side walls are higher than the staple deforming groove.

10. The tissue closure device of claim 9, wherein the staple pushing sheet is provided with a middle wall between the side walls; and the middle wall is lower than the side walls.

11. The tissue closure device of claim 8, wherein there are two closure staples located at the two sides of the cutting knife, respectively.

12. The tissue closure device of claim 7, wherein the cutting knife comprises a cutting portion for cutting off the tissue, as well as a first connection portion and a second connection portion which are respectively located at the two opposite sides of the cutting portion and connected with the cutting portion; and the first and second connection portions selectively disengage from or engage with the staple pushing sheet.

13. The tissue closure device of claim 12, wherein the cutting portion is provided with a halberd blade for cutting off the tissue; and the halberd blade is provided with a tip portion.

14. The tissue closure device of claim 13, wherein the cutting portion is further provided with oblique blades for slidably cutting off side walls of the tissue; each oblique blade extends along a curve, and is smoothly connected with the halberd blade; there are two oblique blades distributed at the two sides of the halberd blade, respectively.

15. The tissue closure device of claim 14, wherein each of the first and second connection portions is provided with a cooperation portion; and the staple pushing sheet is provided with an engagement portion which selectively disengages from or engages with the cooperation portion.

16. The tissue closure device of claim 7, wherein the cutting knife is provided with a cooperation portion; the staple pushing sheet is provided with an engagement portion which selectively disengages from or engages with the cooperation portion; when the staple pushing sheet moves from the staple closure position to the pulling-back position, the cooperation portion cooperates with the engagement portion to enable the staple pushing sheet to drive the cutting knife to move from the distal end of the base to the proximal end, so as to cut off the tissue; and when the staple pushing sheet moves from the original position to the staple closure position, the cooperation portion disengages from the engagement portion.

17. A tissue closure assembly, comprising: the tissue closure device of claim 1, and a closure staple capable of being assembled to the tissue closure device, wherein during a closure process, when the staple pushing sheet is located at the original position, the free end of the closure staple is opposite to the staple pushing sheet; and when the staple pushing sheet is located at the staple closure position, the free end of the closure staple is bent under the action of the staple pushing sheet.

18. The tissue closure assembly of claim 17, wherein the closure staple is provided with an opening portion, a bottom opposite to the opening portion, and a side wall connected to the bottom; and the end of the side wall is spike-shaped.

19. The tissue closure assembly of claim 18, wherein at least one spike-shaped portion is arranged on the bottom of the closure staple.

20. The tissue closure assembly of claim 19, wherein at least one barb whose end point faces the bottom of the closure staple is arranged on the side wall of the closure staple.

21. The tissue closure assembly of claim 17, wherein the closure staple comprises a first side portion, a second side portion opposite to the first side portion, and a bottom connected with the first and second side portions; an opening portion is formed between the first side portion and the second side portion; the bottom is opposite to the opening portion; and at least one thorn portion is arranged on the bottom.

22. The tissue closure assembly of claim 17, wherein the closure staple comprises a base portion, a connection portion connected with the base portion, as well as a first side portion and a second side portion which are connected with the connection portion and are located at the two sides of the connection portion, respectively; an opening is formed between the first side portion and the second side portion; and the base portion constitutes a closed channel allowing an instrument to pass through.

23. The tissue closure assembly of claim 22, wherein the first side portion and the second side portion define a first plane. After the closure staple is bent and formed, projections of bending portions of both the first side portion and the second side portion intersect with each other on the first plane.

24. A medical instrument, comprising: an instrument body, and an firing handle connected to the instrument body, wherein the medical instrument further comprises the tissue closure device of claim 1; and the tissue closure device is detachably connected to the instrument body.

25. The tissue closure device of claim 24, wherein a second accommodating space is formed in the staple accommodating portion, and is communicated with the first accommodating space, the height of the second accommodating space is bigger than the height of the first accommodating space.

26. The tissue closure device of claim 25, wherein the second accommodating space comprises at least one staple accommodating groove; and the staple accommodating groove is capable of accommodating at least part of the closure staple to fix a relative position between the closure staple and the staple accommodating portion.

27. The tissue closure device of claim 24, wherein the staple pushing sheet further comprises a pulling-back position between the original position and the staple closure position; the staple accommodating portion is further configured to place a cutting knife; and when the staple pushing sheet moves from the staple closure position to the pulling-back position, the staple pushing sheet cooperates with the cutting knife to drive the cutting knife to move from the distal end of the base to the proximal end so as to cut off the tissue.

28. The tissue closure device of claim 17, wherein the staple pushing sheet further comprises a pulling-back position between the original position and the staple closure position; the staple accommodating portion is further configured to place a cutting knife; and when the staple pushing sheet moves from the staple closure position to the pulling-back position, the staple pushing sheet cooperates with the cutting knife to drive the cutting knife to move from the distal end of the base to the proximal end so as to cut off the tissue.

29. The tissue closure device of claim 17, wherein there are two closure staples located at the two sides of the cutting knife, respectively.

\* \* \* \* \*